United States Patent [19]
Allen

[11] Patent Number: 5,510,104
[45] Date of Patent: Apr. 23, 1996

[54] METHOD FOR KILLING OR INHABITING THE GROWTH OF SPORULATING MICROORGANISMS WITH HALOPEROXIDASE-CONTAINING COMPOSITIONS

[75] Inventor: Robert C. Allen, San Antonio, Tex.

[73] Assignee: ExOxEmis, Inc., Little Rock, Ark.

[21] Appl. No.: 457,860

[22] Filed: Jun. 1, 1995

Related U.S. Application Data

[62] Division of Ser. No. 343,781, Nov. 22, 1994, Pat. No. 5,451,402, which is a division of Ser. No. 100,780, Aug. 2, 1993, Pat. No. 5,389,369, which is a continuation-in-part of Ser. No. 660,994, Feb. 21, 1991, abandoned.

[51] Int. Cl.$^6$ .................... A61K 38/44; C12N 9/02; C12N 9/04; C12N 9/08
[52] U.S. Cl. ............. 424/94.4; 435/189; 435/190; 435/192; 514/561; 514/564
[58] Field of Search ............ 424/94.4; 435/189, 435/190, 192; 422/28; 514/561, 564

[56] References Cited

U.S. PATENT DOCUMENTS

| | | | |
|---|---|---|---|
| 2,679,533 | 5/1954 | Darragh et al. | 564/282 |
| 4,473,550 | 9/1984 | Rosenbaum et al. | 424/94.4 |
| 4,576,817 | 3/1986 | Montgomery et al. | 424/94 |
| 4,588,586 | 5/1986 | Kessler et al. | 424/94 |
| 4,937,072 | 6/1990 | Kessler et al. | 424/94.4 |
| 4,996,146 | 2/1991 | Kessler | 435/28 |
| 5,389,369 | 2/1995 | Allen et al. | 424/94.4 |
| 5,451,402 | 9/1995 | Allen | 424/94.4 |

FOREIGN PATENT DOCUMENTS

| | | |
|---|---|---|
| 30098073 | 1/1984 | European Pat. Off. . |
| 30361908 | 4/1990 | European Pat. Off. . |
| 10397227 | 11/1990 | European Pat. Off. . |
| 2108387 | 5/1983 | United Kingdom . |
| WO88/02600 | 4/1988 | WIPO . |
| WO89/12457 | 12/1989 | WIPO . |

OTHER PUBLICATIONS

Klebanoff, "Myeloperoxidase–Halide–Hydrogen Peroxide Antibacterial System," *J. Bacteriol.*, 95, 2131–2138, 1968.

Allen, R. C., Dissertation entitled "Studies on the Generation of Electronic Excitation States in Human Polymorphonuclear Leukocytes and their Participation in Microbicidal Activity," Jul., 1973.

Allen, R. C. et al., "Evidence for the Generation of an Electronic Excitation State(s) in Human Polymorphonuclear Leukocytes and its Participation in Bactericidal Activity", *Biochemical and Biophysical Research Communications*, 47(4), 679–684, 1972.

Allen, R. C., "Halide Dependence of the Myeloperoxidase-–mediated Antimicrobial System of the Polymorphonuclear Leukocyte in the Phenomenon of Electronic Excitation", *Biochemical and Biophysical Research Communications*, 63(3), 675–683, 1975.

Allen, R. C., "The Role of pH in the Chemiluminescent Response of the Myeloperoxidase–Halide–HOOH Antimi-crobial System", *Biochemical and Biophysical Research Communications*, 63(3), 684–691, 1975.

Allen, R. C. and L. D. Loose, "Phagocytic Activation of a Luminol–Dependent Chemiluminescence in Rabbit Alveolar and Peritoneal Macrophages", *Biochemical and Biophysical Research Communications*, 69(1), 245–252, 1976.

Allen, R. C., "Evaulation of Serum Opsonic Capacity by Quantitating the Initial Chemiluminescent Response from Phagocytizing Polymorphonuclear Leukocytes", *Infection and Immunity*, 15(3), 828–833, 1977.

Allen, R. C. et al., "Correlation of Metabolic and Chemiluminescent Responses of Granulocytes from Three Female Siblings with Chronic Granulomatous Disease", *Journal of Infectious Diseases*, 136(4), 510–518, 1977.

Allen, R. C., "Reduced, radical, and excited state oxygen in leukocyte microbicidal activity", *In* J. T. Dingle, P. J. Jacques and I. H. Shaw [eds.]. Lysosomes in Applied Biology and Therapeutics, North–Holland Publishing Company, 1979, pp. 197–233.

Allen, R. C., "Chemiluminescence; An Approach to the Study of the Humoral–phagocyte Axis in Host Defense (List continued on next page.)

*Primary Examiner*—Marian C. Knode
*Assistant Examiner*—Susan M. Dadio
*Attorney, Agent, or Firm*—Christensen O'Connor Johnson & Kindness

[57] ABSTRACT

Methods and compositions are provided for killing or inhibiting the growth of yeast or sporular microorganisms by contacting the microorganisms, in the presence of a peroxide and chloride or bromide, with a haloperoxidase and at least one antimicrobial activity enhancing agent. Suitable antimicrobial activity enhancing agents include certain α-amino acids, and are preferably compounds of the formula:

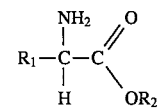

wherein $R_1$ is hydrogen, an unsubstituted, or hydroxy or amino substituted, straight or branched chain alkyl group having from 1 to 6 carbon atoms, or an unsubstituted, or hydroxy or amino substituted arylalky group having from 7 to 12 carbon atoms, and $R_2$ is hydrogen or a straight or branched chain alkyl group having from 1 to 6 carbon atoms. The significantly enhanced haloperoxidase antiyeast and antispore activities make the methods and compositions of the invention highly useful in the therapeutic or prophylactic antiseptic treatment of human or animal subjects and in in vitro applications for disinfection or sterilization of vegetative microbes, yeasts, and bacterial and fungal spores. Suitable haloperoxidases for use in the methods and compositions of the invention include eosinophil peroxidase (EPO) and myeloperoxidase (MPO). Representative antimicrobial activity enhancing agents of the invention include α-amino acids selected from the group consisting of glycine and the l- or d-enantiomers of alanine, valine, leucine, isoleucine, serine, threonine, lysine, phenylalanine, tyrosine, and the alkyl esters thereof.

16 Claims, No Drawings

OTHER PUBLICATIONS

Against Infection", *In Liquid Scintillation Counting, Recent Applications and Development*, vol. II. Sample Preparation and Applications, Academic Press, Inc., 1980, pp. 377–393.

Allen, R. C., et al., "Role of Myeloperoxidase and Bacterial Metabolism in Chemiluminescence of Granulocytes from Patients with Chronic Granulomatous Disease", *Journal of Infectious Diseases*, 144(4), 344–348, 1981.

Allen, R. C. et al., "Humoral–Phagocyte Axis of Immune Defense in Burn Patients", *Archives of Surgery*, 117, 133–140, 1982.

Allen, R. C., "Direct Quantification of Phagocyte Activity in Whole Blood: A Chemiluminigenic Probe Approach", In E. Kaiser, F. Gabl, M. M. Muller and P. M. Bayer [eds.] Proceedings of XI International Congress of Clinical Chemistry, Vienna, 1981. Walter de Gruyter, Berlin, New York, 1982, pp. 1043–1058.

Allen, R. C., "Biochemiexcitation: Chemiluminescence and the Study of Biological Oxygenation Reactions", In W. Adam and G. Cilento [eds.] Chemical and Biological Generation of Excited States, Academic Press, Inc., New York, 1982, pp. 309–344.

Allen, R. C., "Chemiluminescence and the Study of Phagocyte Redox Metabolism", In F. Rossi and P. Patrisica [eds.] Biochemistry and Function of Phagocytes, Plenum Publishing Corporation, 1982, pp. 411–421.

Allen, R. C. and M. M. Lieberman, "Kinetic Analysis of Microbe Opsonification Based on Stimulated Polymorphonuclear Leukocyte Oxygenation Activity", *Infection and Immunity* 45(2), 475–482, 1984.

Allen, R. C., "Phagocytic Leukocyte Oxygenation Activities and Chemiluminescence: A Kinetic Approach to Analysis", In Marlene A. DeLuca and William D. McElroy [eds.] Methods in Enzymology, vol. 133, Bioluminescence and Chemiluminescence, Academic Press, Inc., 1986, pp. 449–493.

Allen, R. C., "Oxygen–Dependent Microbe Killing by Phagocyte Leukocytes: Spin Conservation and Reaction Rate", In W. Ando and Y. Moro–oka [eds.] The Role of Oxygen in Chemistry and Biochemistry, Proceedings of an International Symposium on Activation of Dioxygen and Homogeneous Catalytic Oxidations, Tsukuba, Japan, 12–16 Jul. 1987, *Studies in Organic Chemistry*, vol. 33, pp. 425–434, 1988 Elsevier Science Publishers B.V., Amsterdam.

Steinbeck, M. J., and J. A. Roth, "Neutrophil Activation by Recombinant Cytokines", *Reviews of Infectious Diseases*, 11(4), 549–568, 1989.

Malech, H. L. and J. I. Gallin, "Medical Intelligence, Neutrophils in Human Diseases", *New England Journal of Medicine*, 317(11), 687–694, 1987.

Olsson, I. and P. Venge, "The Role of the Human Neutrophil in the Inflammatory Reaction", *Allergy*, 35 1–13, 1980.

Chenoweth, D. E., "Complement Mediators of Inflammation", In Gordon D. Ross [eds.] Immunobiology of the Complement System, An Introduction for Research and Clinical Medicine, pp. 63–86, Academic Press, 1986.

Fearon, D. T. and L. A. Collins, "Increased Expression of C3b Receptors on Polymorphonuclear Leukocytes Induced by Chemotactic Factors and By Purification Procedures", *J. Immunology* 130(1), 370–175, 1983.

Fearon, D. T. and W. W. Wong, "Complement Ligand–Receptor Interactions that Mediate Biological Responses", *Ann. Rev. Immunol.* 1, 243–271, 1983.

Kearns, D. R. and A. U. Khan, "Sensitized Photooxygenation Reactions and the Role of Singlet Oxygen", *Photochemistry and Photobiology*, 10, 193–219, 1969.

Kanofsky, J. R., "Singlet Oxygen Production by Lactoperoxidase", *Journal of Biological Chemistry*, 258(10), 5991–5993, 1983.

Lehrer, R. I., "Antifungal Effects of Peroxidase Systems,", *J. Bacteriol.* 99(2), 361–365, 1969.

Klebanoff, S. J. et al., "The Peroxidase–Thiocyanate–Hydrogen Peroxide Antimicrobial System", *Biochimica et Biophysica Acta*, 117, 63–72, 1966.

Klebanoff, S. J., "Myeloperoxidase–Halide–Hydrogen Peroxide Antibacterial System", *J. Bacteriol.* 95(6), 2131–2138, 1968.

Klebanoff, S. J., "Myeloperoxidase–mediated Antimicrobial Systems and their Role in Leukocyte Function", reprinted from *Biochemistry of the Phagocytic Process*, Julius Schultz ed., (North–Holland Publishing Company, 1970), reprinted.

Klebanoff, S. J. et al., "Toxic Effect of the Peroxidase–Hydrogen Peroxide–Halide Antimicrobial System on *Mycobacterium leprae*", *Infect. and Immun.* 44(2), 534–536, 1984.

Hamon, C. B. et al., "A Peroxidase–mediated, *Streptococcus mitis*–dependent antimicrobial system in saliva", *J. Exp. Med.* 137, 438–450, 1973.

Belding, M. E. et al., "Peroxidase–Mediated Virucidal Systems", *Science* 167, 195–196, 1970.

Steele, W. F. et al., "Antistreptococcal Activity of Lactoperoxidase", *J. Bacteriol.* 97(2), 635–639, 1969.

Mickelson, M. N., "Effect of Lactoperoxidase and Thiocyanate on the Growth of *Streptococcus pyogenes* and *Streptococcus agalactiae* in a Chemically Defined Culture Medium", *J. gen Microbiol.* 43, 31–43, 1966.

Yanagita, T., "Biochemical Aspects on the Germination of Conidiospores of Aspergillus niger," *Archiv. für Mikrobiologic.* 26, 329–344, 1957.

Halvorson, H. et al., "Biochemistry of Spores of Aerobic Bacilli With Special Reference to Germination," *Bac. Rev.* 21 112–131, 1957.

Smith, A. G. et al., "Application of Cholesterol Oxidase in the Analysis of Steroids," *J. of Chrom.* 101, 373–378, 1974.

Richmond, W., "Preparation and Properties of a Cholesterol Oxidase from *Nocardia sp.* and Its Application to the Enzymatic Assay of Total Cholesterol in Serum," *Clin. Chem.* 19/12, 1350–1356, 1973.

Weete, J. D., "Review Article, Sterols of the Fungi: Distribution and Biosynthesis," *Physiochemistry* 12, 1843–1864, 1973.

Darrell, J. et al., "Lipid Metabolism of Fungal Spores," in International Fungal Spore Symposium, 2d, Brigham Young University, 1974, John Wiley & Sons, Inc., pp. 178, 180, 1976.

Lingappa, B. T., et al., "Phenethyl Alcohol Induced Germination of Ascospores of *Neurospora*," *Arch. Mikrobiol.* 72, 97–105, 1970.

Sussman, A. S. et al., "Activation of Neurospora Ascospores by Organic Solvents and Furans," *Mycologia* 51, 237–247, 1959.

Biosis Abstract, Clark et al., "Peroxidase–H2O2–halide system: Cytotoxic effect on mammalian tumor cells," *Blood* 45(2), 161–170, 1975.

Biological Abstract No. 65021608; Rosen, H. et al., "Formation of Singlet oxygen by the Myelo Peroxidase Mediated Anti Microbial System" *J. Biol. Chem.* 252(14), 4803–4810, 1977.

Biological Abstract No. 82079537; Thomas, E. L. et al.,

"Oxidation of Chloride and thiocyanate by isolated leukocytes," *J. Biol. Chem.* 261(21), 9694–9702, 1986.

Paul, B. B. et al., "Role of the Phagocyte in Host–Parasite Interactions," *Infection and Immunity* 2(4):414–418, 1970.

Strauss, R. R. et al., "Role of the Phagocyte in Host–Parasite Interactions XXII. $H_2O_2$–Dependent Decarboxylation and Deamination by Myeloperoxidase and Its Relationship to Antimicrobia Activity," *Res.–Journal of Reticuloendothelial Society* 7:754–761, 1970.

Zgliczynski, J. M. et al., "Myeloperoxidase of Human Leukaemic Leucocytes," *European J. Biochem.* 4:540–547, 1968.

Hills, G. M., "Chemical Factors in the Germination of Spore–bearing Aerobes: Observations on the Influence of Species, Strain and Conditions of Growth," *J. Gen. Microbiol.* 4:38–47, 1950.

Klebanoff, S. J., "Antimicrobial Mechanisms in Neutrophilic Polymorphonuclear Leukocytes," *Seminars in Hematology* 12(2):117–142, 1975.

METHOD FOR KILLING OR INHIBITING THE GROWTH OF SPORULATING MICROORGANISMS WITH HALOPEROXIDASE-CONTAINING COMPOSITIONS

This application is a divisional of prior application Ser. No. 08/343,781, filed on Nov. 22, 1994, now U.S. Pat. No. 5,451,402, which in turn is a divisional of application Ser. No. 08/100,780, filed Aug. 2, 1993, now U.S. Pat. No. 5,389,369, which in turn is a continuation-in-part of application Ser. No. 07/660,994, filed on Feb. 21, 1991, now abandoned, the benefit of the filing dates of which are hereby claimed under 35 U.S.C. 120.

FIELD OF THE INVENTION

The present invention relates to methods and compositions for the killing of yeasts and sporular forms of microbes. More particularly, the present invention relates to methods and compositions using a combination of an antimicrobial activity enhancing agent and haloperoxidase to enhance microbicidal properties of the system.

BACKGROUND OF THE INVENTION

As disclosed in PCT application Publication Number WO 92/14484, haloperoxidases, such as myeloperoxidase and eosinophil peroxidase, may be used to selectively bind to and, in the presence of peroxide and halide, inhibit the growth of target microorganisms without eliminating desirable microorganisms of significantly damaging other components of the medium, such as host cells and normal flora, in the target microorganism's environment. Myeloperoxidase and eosinophil peroxidase have previously been known to exhibit microorganism killing activity in natural systems when presented with an appropriate halide cofactor ($X^-$) and hydrogen peroxide as substrate (Klebanoff, 1968, *J. Bacteriol.* 95:2131–2138). However, the selective nature of haloperoxidase binding and the utility of these systems for therapeutic, research and industrial applications has only recently been recognized. Due to the newly discovered selective binding properties of haloperoxidases, when a target microorganism, such as a pathogenic microorganism, has a binding capacity for haloperoxidase greater than that of a desired microorganism, such as members of the normal flora, the target microorganism selectively binds the haloperoxidase with little or no binding of the haloperoxidase by the desired microorganism. In the presence of peroxide and halide, the target bound haloperoxidase catalyzes halide oxidation and facilitates the disproportionation of peroxide to singlet molecular oxygen ($^1O_2$) at the surface of the target microorganism, resulting in selective killing of the target microorganism with a minimum of collateral damage to the desired microorganism or physiological medium. Thus, as disclosed in PCT application Publication Number WO 92/14484, myeloperoxidase and eosinophil peroxidase can be employed as antiseptics in the therapeutic or prophylactic treatment of human or animal subjects to selectively bind to and kill pathogenic microorganisms with a minimum of collateral damage to host cells and normal flora of the host.

The system may also be employed in disinfecting or sterilizing formulations for inhibiting the growth of target microorganisms in vitro, particularly in applications where biomedical devices, such as bandages, surgical instruments, suturing devices, catheters, dental appliances, contact lenses and the like, are antiseptically treated to inhibit the growth of target microorganisms without damage to host cells of a subject when the biomedical device is subsequently utilized in vivo. While the haloperoxidase antiseptic system disclosed in PCT application Publication Number WO 92/14484 has been found to be highly effectively in the treatment of pathogenic microbes, yeast and some spore forming microorganisms remain relatively immune to haloperoxidase antimicrobial activity.

The spore stage of the microbial life cycle is characterized by metabolic dormancy and resistance to environmental factors that would destroy the microbe in its vegetative stage. The earliest phase of spore germination is characterized by swelling and a shift from dormancy to active metabolism. Vegetative growth, e.g., sprouting, and ultimately reproduction follows.

Germination of bacterial endospores and fungal spores is associated with increased metabolism and decreased resistance to heat and chemical reactants. For germination to occur, the spore must sense that the environment is adequate to support vegetation and reproduction. The amino acid l-alanine is reported to stimulate bacterial spore germination (Hills, 1950, *J Gen Microbiol* 4:38; Halvorson and Church, 1957, *Bacteriol Rev* 21:112). L-alanine and l-proline have also been reported to initiate fungal spore germination (Yanagita, 1957, *Arch Mikrobiol* 26:329).

Simple $\alpha$-amino acids, such as glycine and l-alanine, occupy a central position in metabolism. Tranamination or deamination of $\alpha$-amino acids yields the glycogenic or ketogenic carbohydrates and the nitrogen needed for metabolism and growth. For example, transamination or deamination of l-alanine yields pyruvate which is the end product of glycolytic metabolism (Embden-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple $\alpha$-amino acids can provide the nitrogen, $CO_2$, glycogenic and/or ketogenic equivalents required for germination and the metabolic activity that follows.

Zgliczxnski et al. (1968, *European J. Biochem* 4:540–547) reported that myeloperoxidase catalyzes the chloride-dependent oxidation of amino acids by hydrogen peroxide to yield ammonia, carbon dioxide and an aldehyde corresponding to the decarboxylated, deaminated amino acid, and Strauss et al. (1970, *J Reticuloendothel Soc* 7:754–761) postulated that the aldehydes so produced might serve as microbicidal agents. However, Paul et al. (1970, *Infect Immun* 2:414–418) reported that adding the $\alpha$-amino acids glycine and l-alanine to a myeloperoxidase-hydrogen peroxide-chloride test system actually inhibited killing of *Escherichia coli*. Furthermore, Klebanoff (1975, *Semin Hemat* 12:117–142) reported that 100 mM acetaldehyde was required for bactericidal action. Contrary to these published data, it has now been surprisingly discovered that the microbicidal action of haloperoxidases against yeast and sporular forms of microbes may be significantly enhanced by treating the microorganisms with haloperoxidase in combination with certain $\alpha$-amino acids which serve as an antimicrobial activity enhancing agent.

SUMMARY OF THE INVENTION

In accordance with the present invention, methods and compositions are provided for killing or inhibiting the growth of yeast or sporular microorganisms comprising contacting the microorganisms, in the presence of a peroxide and chloride or bromide, with a haloperoxidase and at least one antimicrobial activity enhancing agent. Suitable antimicrobial activity enhancing agents include certain α-amino acids, and are preferably compounds of the formula:

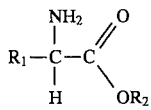

wherein $R_1$ is hydrogen, an unsubstituted, or hydroxy or amino substituted, straight or branched chain alkyl group having from 1 to 6 carbon atoms, or an unsubstituted, or hydroxy or amino substituted arylalky group having from 7 to 12 carbon atoms, and $R_2$ is hydrogen or a straight or branched chain alkyl group having from 1 to 6 carbon atoms. In one embodiment, the methods and compositions of the invention may be used to kill yeast and sporular microbes in vitro, to disinfect or sterilize medical products or materials. In other embodiments, the methods and compositions can be employed in the antifungal and antiyeast treatment of human or animal subjects without eliminating desirable microorganisms or significantly damaging host cells. It has been discovered that the antiyeast and antifungal spore activities of haloperoxidases are significantly enhanced in the presence of certain α-amino acids. In the further presence of peroxide and halide, the target bound haloperoxidase catalyzes halide oxidation and facilitates the disproportionation of peroxide to singlet molecular oxygen at the surface of the spore forming microorganism, resulting in killing of the target microorganism. Although it is likely that haloperoxidase activity will catalyze the deamination, decarboxylation of a portion of the added α-amino acids to yield aldehydes, it is unlikely that such aldehydes significantly contribute to microbicidal action at such low concentrations. It is likely that these α-amino acids exert a mild concentration-dependent competitive inhibition of microbicidal action by consuming a portion of the haloperoxidase generated hypochlorous acid and singlet molecular oxygen. However, the stimulating effect of these α-amino acids on yeast budding, germination of sporulated microbes, and possibly acceleration of metabolism of vegetative microbes appears to labilize the microbes so treated to the actions of haloperoxidases and thus greatly enhance microbicidal action.

The significantly enhanced haloperoxidase antiyeast and antispore activities make the methods and compositions of the invention highly useful in the therapeutic or prophylactic antiseptic treatment of human or animal subjects and in in vitro applications for disinfection and sterilization of vegetative microbes, yeasts, and bacterial and fungal spores.

Suitable haloperoxidases for use in the methods and compositions of the invention include eosinophil peroxidase (EPO) and myeloperoxidase (MPO). Representative antimicrobial activity enhancing agents of the invention include α-amino acids selected from the group consisting of glycine and the l- or d-enantiomers of alanine, valine, leucine, isoleucine, serine, threonine, lysine, phenylalanine, tyrosine, and the alkyl esters thereof.

DETAILED DESCRIPTION OF THE PREFERRED EMBODIMENT

The present invention is broadly directed to methods and compositions for the killing or inhibition of yeast and sporulated microorganisms using a haloperoxidase and an antimicrobial activity enhancing agent which labilizes the yeast and spore forms of the microorganism to haloperoxidase microbicidal activity. In the practice of the invention, yeast and spore forms of microorganisms are killed or inhibited by contacting the microorganisms with amounts of a haloperoxidase and an antimicrobial activity enhancing agent, i.e., certain α-amino acids, which are effective in the presence of a peroxide and bromide or chloride, to inhibit the growth of or kill the microorganisms.

In one particularly preferred embodiment, the methods and compositions of the invention are used as antiseptic agents exhibiting enhanced haloperoxidase antispore and antiyeast activity against a broad range of pathogenic microorganisms including bacteria and fungi. For use in contact with host tissue, the antiseptic systems are based on the use of dioxygenating haloperoxidase enzymes which exhibit selective affinity for pathogenic microorganisms. As such, high potency microbicidal action can be directed to the target microorganisms without associated host tissue destruction or disruption of normal flora; i.e., the antiseptic action is selective and confined to the target microorganism.

When properly formulated, haloperoxidase-enhancer preparations can be employed to disinfect and even sterilize materials and devices. High potency haloperoxidase-enhancer formulations can serve as in vitro disinfecting or sterilizing preparations. By limiting the time period of hydrogen peroxide availability, haloperoxidase-enhancer formulations can be made sufficiently potent to insure disinfection and even sterilization of a material or device before contact with host tissue. Any potential toxicity to normal flora and host tissue associated with the use of these high potency formulations will cease when peroxide is depleted, and as such, the formulation-treated material or device can be brought in contact with host tissue without additional washing to detoxification.

Representative compositions of the invention comprise (1) eosinophil peroxidase (EPO) and/or myeloperoxidase (MPO), (2) hydrogen peroxide ($H_2O_2$) or equivalent peroxide, or an oxidase for the generation of $H_2O_2$, (3) a substrate for the oxidase, and (4) an antimicrobial activity enhancing agent, such as glycine or l-alanine.

In one presently preferred embodiment, the invention provides methods and compositions for inhibiting the growth of yeast and sporular microorganisms in vitro, particularly in applications where biomedical devices, such as bandages, surgical instruments, suturing devices, catheters, dental appliances, contact lenses and the like, require disinfection or sterilization and where the device is to be subsequently contacted with host tissue. The methods and compositions of the invention may also be used to treat or prevent infections by yeast or spore forming microorganisms in vivo.

Haloperoxidases useful in the present invention are defined as halide:hydrogen peroxide oxidoreductases (e.g., EC No. 1.11.1.7 and EC No. 1.11.1.10 under the International Union of Biochemistry) for which halide, i.e., chloride or bromide, is the electron donor or reductant and peroxide is the electron receiver or oxidant. Any haloperoxidase which catalyzes the halide dependent generation of singlet molecular oxygen from hydrogen peroxide and which exhibits selective binding to target microorganisms may be used in the present invention. Presently particularly preferred haloperoxidases, as demonstrated herein, include eosinophil peroxidase (EPO), myeloperoxidase (MPO) and combinations thereof. Inclusion of an antimicrobial enhancing agent, as described in detail herein, greatly increases the microbicidal capacity of the oxidase-haloperoxidase system against yeast and sporular microorganisms since it labilizes these forms to the microbicidal action of the haloperoxidase system.

Antimicrobial activity enhancing agents of the invention are agents that enhance the antimicrobial activity of the haloperoxidase antimicrobial system against yeast and sporular microorganisms, used at concentrations that do not produce adverse effects on the haloperoxidase activity of the system or undesirable effects in the environment of use of the methods and compositions. Presently preferred activity enhancing agents of the invention include α-amino acid compounds of the formula:

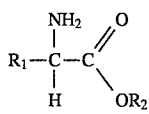

wherein $R_1$ is hydrogen, a straight or branched chain alkyl group having from 1 to 6 carbon atoms, or an unsubstituted or hydroxy or amino substituted straight or branched chain arylalky group having from 7 to 12 carbon atoms, and $R_2$ is hydrogen or a straight or branched chain alkyl group having from 1 to 6 carbon atoms. As used herein, amino acids may be in their acid form, as shown above, or may be in their zwitterionic form represented by the formula:

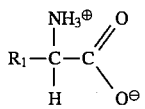

wherein $R_1$ and $R_2$ having the meanings set forth above, and may be in either l- or d-enantiomeric configurations. Representative alkyl $R_1$ groups include, for example, methyl, hydroxymethyl, isopropyl, 2-isobutyl, 1-isobutyl, hydroxy ethyl and amino butyl groups. Representative arylalkyl $R_1$ groups include, for example, tolyl and hydroxytolyl groups. Presently particularly preferred alkyl $R_2$ groups include methyl and ethyl groups. Representative antimicrobial activity enhancing agents of the invention include α-amino acids selected from the group consisting of glycine and the l- or d-enantiomers of alanine, valine, leucine, isoleucine, serine, threonine, lysine, phenylalanine, tyrosine and the alkyl esters thereof. The presently most preferred antimicrobial activity enhancing agents are glycine and l-alanine.

The nature and thickness of the spore wall affords protection against the lethal action of singlet molecular oxygen and hypochlorous acid. With respect to fungal spores, α-amino acid induced spore germination yields vegetative forms that are more susceptible to oxidants. In addition, it has been found that the antimicrobial activity enhancing agents of the invention also increase oxidase-haloperoxidase killing of yeast vegetative forms, including Candida albicans (see Table 1, below). This phenomenon may be related to the α-amino acid-dependent acceleration of yeast growth and budding, and the increased susceptibility of such metabolically active forms to haloperoxidase killing. One alternative possibility is that α-amino acids, or metabolic products thereof, act as a substrate for a fungal oxidase capable of generating $H_2O_2$. Another alternative possibility is that the aldehyde products of haloperoxidase-mediated α-amino acid deamination-decarboxylation might induce germination and budding, or otherwise effect some vital process.

Since the antiseptic activity of the haloperoxidase compositions of the invention involves the reaction of peroxide and bromide or chloride to form hypohalite, and the reaction of peroxide and hypohalite to form singlet molecular oxygen, the activity of the compositions of the invention is dependent upon the presence, at the site of antimicrobial activity, of a suitable peroxide and halide. In some situations, peroxide (e.g., hydrogen peroxide) may be present at the site of antimicrobial activity due, for example, to the activity of naturally occurring flora, and sufficient amounts of chloride may be present in the physiological milieu to act as a cofactor in the conversion reaction. In these situations, no additional peroxide or halide need be administered or included in the compositions of the invention. In other situations, it may be necessary to additionally provide hydrogen peroxide and/or halide at the site of microbial treatment. Accordingly, the compositions of the invention may additionally comprise, if desired, a peroxide or agent capable of producing peroxide in vivo or in vitro and a halide.

Peroxides useful in the methods and compositions of the invention include hydrogen peroxide, alkyl hydroperoxides of the formula:

wherein R is a hydrogen or a short chain alkyl group having from 1 to 3 carbon atoms, and inorganic peroxides, such as boroperoxide or ureaperoxide. The oxidant activity of the organic peroxides generally decreases with increasing R chain length, as follows:

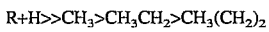

The presently preferred peroxide for use in the compositions of the invention is hydrogen peroxide. Hydrogen peroxide may also be made available at the site of the antimicrobial activity by including in the composition an agent capable of producing hydrogen peroxide in vivo or in vitro. Particularly useful agents for this purpose include, for example, oxidases, such as cholesterol oxidase, glucose oxidase and galactose oxidase.

When hydrogen peroxide is directly included in compositions of the invention for in vivo applications, the amounts employed are preferably designed to provide maximum disinfecting activity. Damage to host cells and tissue and to normal flora is avoided by avoiding direct contact during the period of high $H_2O_2$ exposure. Accordingly, when included in liquid formulations, the compositions of the invention may comprise from about 1 nmol to about 10 µmol of hydrogen peroxide per ml of liquid composition, more preferably from about 5 nmol to about 5 µmol of hydrogen peroxide per ml of liquid composition, and most preferably from about 10 nmol to about 1 µmol of hydrogen peroxide per ml of liquid composition. Agents capable of producing hydrogen peroxide in vivo, e.g., peroxide producing oxidases, are particularly useful for dynamic control of the amounts of hydrogen peroxide present at the site of antimicrobial activity. Such agents maximize antimicrobial activity of the composition by providing and maintaining a steady, low level concentration of $H_2O_2$. Accordingly, the amount of such agents to be employed will be highly dependent on the nature of the agent and the effect desired, but will preferably be capable of producing a steady state level of from about 1 pmol to about 1 µmol of hydrogen peroxide per ml of liquid per minute, depending on the type and concentration of halide available at the site of antimicrobial activity. When the formulation is to be used as a disinfectant-sterilizing solution, the oxidase and its substrate can be adjusted to provide relatively high steady-state concentrations of $H_2O_2$ lasting for the required sterilization period. The disinfection-sterilizing action is terminated with exhaustion of the oxidase substrate or relative to the rate of oxidase degradation.

For antifungal purposes, the use of cholesterol oxidase, e.g., from *Nocardia erythropolis*, as a $H_2O_2$ producing oxidase is presently particularly preferred. Unlike prokaryotic bacteria, fungi synthesize sterols. In fact, the antifungal activity of amphotericin B is at least in part dependent on binding to fungal membrane steroids, e.g., ergosterol. Ergosterol is the predominant sterol constituent of most fungi, but other sterols are present (Weete, 1973, *Phytochemistry* 12:1843). Cholesterol oxidase from *Nocardia erythropolis* selectively oxidizes $\Delta^5$-3β-ols and 5α-3β-ols to the resulting ketones (Smith and Brooks, 1974, *J Chromatography* 101:373); e.g.,

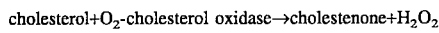

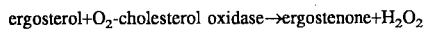

This Nocardia oxidase is relatively heat stable and retains catalytic activity at 50° C. It is active over a pH range of 4 to 9 with a maximum activity at pH 7. It has a Michaelis constant (Km) of $1.4 \times 10^{-5}$ mol/liter (Richmond, 1973, *Clin Chem.* 19:1350).

Haloperoxidases are fungicidal when presented with $H_2O_2$ or coupled to a $H_2O_2$-generating oxidase. However, with cholesterol oxidase as the oxidase, oxidase-haloperoxidase fungal killing is greater than expected from the generation of $H_2O_2$ alone. This cholesterol oxidase-dependent increase in fungicidal action may in part be related to disruption of fungal membrane integrity resulting from oxidase depletion of fungal steroids. Fungi might also synthesize an endogenous $H_2O_2$-generating sterol oxidase Suitable halides for use in the methods and compositions of the invention may be bromide or chloride. The use, selection, and amount of halide employed in a particular application will depend upon various factors, such as the haloperoxidase used in the antiseptic composition, the desired therapeutic effect, the availability of peroxide and other factors. When the haloperoxidase is myeloperoxidase, the halide may be bromide or chloride. Since chloride is present in most physiological media at levels sufficient to be nonlimiting as the halide cofactor, an external source of chloride is generally not required. When an external source of chloride is desired, the amount of chloride employed will preferably fall in the range of about 10 μmol chloride to about 150 μmol chloride per ml of solution to approximate physiological conditions.

When the haloperoxidase is eosinophil peroxidase, chloride is relatively ineffective as a cofactor, and accordingly, the preferred halide is bromide. When included in liquid compositions, the compositions of the invention may comprise from about 1 nmol bromide to about 20 μmol bromide per ml of liquid composition, more preferably from about 10 nmol bromide to about 10 μmol bromide per ml of liquid composition, and most preferably from about 100 nmol bromide to about 1 μmol bromide per ml of liquid composition.

The ratio of halide to peroxide is an important consideration in formulating an effective microbicidal environment. Accordingly, in addition to ensuring effective levels of halide and peroxide at the situs of microbial attack, as described above, it is preferable to practice the methods of the invention at halide peroxide ratios that provide optimal microbicidal activity. For example, when the haloperoxidase is MPO and the halide is $Cl^-$, the ratio of $Cl^-$ to peroxide is preferably maintained in the range of about 1 to about 40,000 in the environment of microbicidal activity, more preferably from about 50 to about 40,000 and most preferably from about 200 to about 40,000. When the halide is $Br^-$, the ratio of $Br^-$ to peroxide is preferably maintained in the range of about 0.1 to about 4,000 in the environment of microbicidal activity, more preferably from about 0.5 to about 2,000 and most preferably from about 1 to about 1,000.

The methods and compositions of the invention can be used to inhibit the growth of a broad spectrum of sporular microorganisms, preferably with a minimum of damage to normal flora. As used herein, "sporular microorganisms" is intended to include spore forms of bacteria or fungi. Spore forming microorganisms are well known, and include, for example, bacteria such as Bacillus sps. and Clostridium sps., and fungi such as Aspergillis sps., Fusarium sps., Trichophyton sps. and the like.

As used herein, the term "normal flora" means bacteria which normally reside in or on body surfaces of a healthy host at symbiotic levels. Normal flora include, for example, the lactic acid family of bacteria in the mouth, intestine, or vagina of human subjects, e.g. Streptococcus (viridans) in the mouth, and Lactobacillus sp. (e.g., Tissier's bacillus and Doderlein's bacillus) in the intestines of breast-fed infants, external genitalia, anterior urethra and vagina. Microorganisms which constitute normal flora of a host are well known (e.g., see *Principles and Practice of Infectious Diseases*, supra, New York, pp. 34–36 and 161). It has been found that the haloperoxidases of the invention selectively bind to many pathogenic bacteria and fungi in preference over normal flora. In in vivo applications, the host is preferably treated with an amount of haloperoxidase which is ineffective to eliminate normal flora from the host. In in vitro applications for disinfection-sterilization, sufficiently high concentrations of haloperoxidase can be employed to ensure complete killing of all vegetative and yeast forms. Under such conditions, damage to host tissue and normal flora is avoided by consumption of $H_2O_2$ or the $H_2O_2$-generating system prior to contact with the host tissue.

The compositions of the invention generally comprise amounts of a haloperoxidase and of an antimicrobial activity enhancing agent which are effective, in the presence of a peroxide and a halide to kill or inhibit the growth of yeast or sporular microorganisms. The compositions may be conveniently provided in a liquid carrier. Any liquid carrier may be generally used for this purpose, provided that the carrier does not significantly interfere with the selective binding capabilities of the haloperoxide or with enzyme activity. Alternatively, the compositions may be provided in solid form with activation on solubilization in liquid.

The compositions of the invention may additionally comprise peroxide or an agent capable of producing peroxide, such as an oxidase, as described in detail above. The oxidase-haloperoxidase system lends itself to construction as a binary formulation. One part of the binary comprises a solution containing the oxidase, the haloperoxidase and the antimicrobial activity enhancing substance, e.g., glycine or l-alanine. The second part of the binary comprises a substrate for the oxidase, e.g., cholesterol in the case of cholesterol oxidase or molecular oxygen, $O_2$. The substrate may be provided, for example, in the form of a solid wafer. For sterilization of an article, e.g., a contact lens, the cholesterol wafer is placed in a sterilization chamber along with the item to be sterilized. The cholesterol oxidase-haloperoxidase plus glycine or l-alanine solution is added to initiate sterilization. This composition may additionally comprise alcohol in order to facilitate cholesterol solubilization and utilization by the oxidase. This system will produce sustained microbicidal action as long as sufficient cholesterol is present to drive the reaction.

For in vivo applications, the antiseptic compositions can be administered in any effective pharmaceutically acceptable form to warm blooded animals, including human and animal subjects, e.g., in topical, lavage, oral or suppository dosage forms, as a topical, buccal, or nasal spray or in any other manner effective to deliver active haloperoxidase to a site of microorganism infection. The route of administration will preferably be designed to obtain direct contact of the antiseptic compositions with the infecting microorganisms.

For topical applications, the pharmaceutically acceptable carrier may take the form of liquids, creams, foams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Solid dosage forms for oral or topical administration include capsules, tablets, pills, suppositories, powders, and granules. In solid dosage forms, the compositions may be admixed with at least one inert diluent such as sucrose, lactose, or starch, and may additionally comprise lubricating agents, buffering agents, enteric coatings, and other components well known to those skilled in the art.

In another embodiment of the invention, the compositions of the invention may be specifically designed for in vitro applications, such as disinfecting or sterilization of medical devices, contact lenses and the like, particularly where the devices or lenses are intended to be used in contact with a patient or wearer. For applications of this type, the compositions may be conveniently provided in the form of a liquid or foam, and may be provided with emulsifiers, surfactants, buffering agents, wetting agents, preservatives, and other components commonly found in compositions of this type. Compositions of the invention may be impregnated into absorptive materials, such as sutures, bandages, and gauze, or coated onto the surface of solid phase materials, such as staples, zippers and catheters to deliver the compositions to a site for the prevention of microbial infection. Other delivery systems of this type will be readily apparent to those skilled in the art.

Actual amounts of haloperoxidase and antimicrobial activity enhancing agents in the compositions of the invention may be varied so as to obtain amounts of haloperoxidase and antimicrobial activity enhancing agents at the site of treatment effective to kill vegetative as well as yeast and sporular microorganisms. Accordingly, the selected amounts will depend on the nature and site for treatment, the desired response, the desired duration of microbicidal action and other factors. Generally, when the haloperoxidase is myeloperoxidase, liquid compositions of the invention will comprise at least 0.01 picomoles (pmol) of myeloperoxidase per ml of liquid composition, more preferably from about 0.1 pmol to about 500 pmol of myeloperoxidase per ml of liquid composition, and most preferably from about 0.5 pmol to about 50 pmol of myeloperoxidase per ml of liquid composition. Similar dosages of eosinophil peroxidase may be employed. Optionally, it may be desirable in some applications to include both eosinophil peroxidase and myeloperoxidase in the same composition. Liquid compositions of the invention will generally comprise at least 0.005 µmol/ml of antimicrobial activity enhancing agents, i.e., $\alpha$-amino acids such as glycine and alanine, and more preferably from 0.05 µmol/ml to 50 µmol/ml of such antimicrobial activity enhancing agent.

Other components, such as an oxidase for peroxide generation, substrate for the oxidase and halide may be included, as desired, as described in detail above. In addition, the components may be formulated in a single formulation, or may be separated into binary formulations for later mixing during use, as may be desired for a particular application. For single formulations, one required system component which is available at the application site, such as halide, oxidase, prosthetic group for the oxidase, reducing substrate for the oxidase, or molecular oxygen is preferably left out of the formulation to preclude premature reaction and exhaustion of system components.

As an illustrative example, a composition suitable for use as a contact lens solution may comprise from 1 to 20 pmol/ml of eosinophil peroxidase and/or myeloperoxidase, from 0.1 to 1 µmol/ml of glycine, from 0.01 to 10 units of glucose oxidase, and from 50 to 500 mEq/L of chloride with 0.1 to 1 mEq/L bromide. The above composition is combined with from 1 to 10 µmol/ml of glucose under anaerobic conditions and the complete preparation is kept anaerobic until used as a liquid disinfectant or sterilizing solution. Exposure to air, i.e., molecular oxygen, activates the disinfecting-sterilizing action of the formulation.

The foregoing may be better understood in connection with the following representative examples, which are presented for purposes of illustration and not by way of limitation.

EXAMPLES

Example 1

The Effect of l-Alanine on Oxidase-Haloperoxidase Killing of Bacterial, Yeast and Fungal Spores The effect of l-alanine on oxidase-haloperoxidase killing of bacterial, yeast and fungal spores was determined as follows. Incubation media was prepared from 50 mM acetate buffer containing 0.1 unit (i.e., 4 µg) cholesterol oxidase from *Nocardia erythropolis* (prepared in accordance with the procedure of Richmond, W., "Preparation and Properties of a Cholesterol Oxidase from Nocardia sp. and Its Application to the Enzymatic Assay of Total Cholesterol in Serum," *Clin. Chem.* 19(12):1350–1356 (1973), 20 pmol (2.8 µg) porcine MPO (ExOxEmis, Inc., San Antonio, Tex. U.S.A., Lot#1899201) or 20 pmol (1.5 µg) porcine EPO (ExOxEmis, Inc., San Antonio, Tex., U.S.A., Lot#1929201), 100 mEq/L $Cl^{31}$, and 1 mEq/L $Br^-$. Incubation mixtures were prepared by inoculating the incubation media with $1\times10^7$ cells of *Staph. aureus, Cand. albicans*, and *Asperg. fumigatus*. The pH of the incubation mixtures was adjusted to 7 with 50 mM MOPS buffer. Cholesterol in 8.5% ethanol was added to the incubation mixtures to a final concentration of 7 mM (7 µmol/ml). The final volume of the incubation mixtures was 1 ml. The mixtures were incubated for four hours at 22° C. and the microbes were then plated (*S. aureus* was plated on trypticase soy agar; *C. albicans* and *A.* fumigatus were plated on Sabouraud's dextrose agar). After about 24 hours (about 72–96 hours for *A. fumigatus*), the colony forming units (CFU) were counted as a measure of the viability of the organisms. The results are shown in Table 1.

TABLE 1

Effect of l-Alanine on Cholesterol Oxidase-Haloperoxidase Microbicidal Action Against *Staphylococcus aureus*, *Candida albicans*, and *Aspergillus fumigatus* Spores:

| Organism | Cholesterol Oxidase | Haloperoxidase | CFU |
|---|---|---|---|
| Staph. aureus | None | None | 19,400,000 |
| Staph. aureus | 0.1 Unit | None | 29,000,000 |
| Staph. aureus | 0.1 Unit † | None | 29,200,000 |
| Staph. aureus | 0.1 Unit | 20 pmol MPO | 0 |
| Staph. aureus | 0.1 Unit † | 20 pmol MPO | 0 |
| Staph. aureus | 0.1 Unit | 20 pmol EPO | 0 |
| Staph. aureus | 0.1 Unit † | 20 pmol EPO | 0 |
| Cand. albicans | None | None | 1,460,000 |
| Cand. albicans | 0.1 Unit | None | 1,380,000 |
| Cand. albicans | 0.1 Unit † | None | 1,580,000 |
| Cand. albicans | 0.1 Unit | 20 pmol MPO | 800,000 |
| Cand. albicans | 0.1 Unit † | 20 pmol MPO | 0 |
| Cand. albicans | 0.1 Unit | 20 pmol EPO | 680,000 |
| Cand albicans | 0.1 Unit † | 20 pmol EPO | 0 |
| Asperg. fumigatus | None | None | 1,260,000 |
| Asperg. fumigatus | 0.1 Unit | None | 1,020,000 |
| Asperg. fumigatus | 0.1 Unit † | None | 880,000 |
| Asperg. fumigatus | 0.1 Unit | 20 pmol MPO | 550,000 |
| Asperg. fumigatus | 0.1 Unit † | 20 pmol MPO | 0 |
| Asperg. fumigatus | 0.1 Unit | 20 pmol EPO | 840,000 |
| Asperg. fumigatus | 0.1 Unit † | 20 pmol EPO | 0 |

†indicates that the 50 mM Acetate Buffer contained 1 mM l-alanine.

As shown in Table 1, cholesterol oxidase plus either MPO or EPO provides a potent microbicidal system. This combination killed $10^7$ *Staphylococcus aureus* in the presence or absence of 1 mM l-alanine. However, inclusion of l-alanine in the cholesterol oxidase-haloperoxidase system was necessary for complete killing of both *Candida albicans* yeast forms and *Aspergillus fumigatus* spores.

Example 2

Effect of Potential Amino Acid Antimicrobial Activity Enhancing Agents on Haloperoxidase Microbicidal Action Against *Aspergillus fumigatus* Spores The effect of various potential amino acids as enhancing agents for haloperoxidase microbicidal action was determined by following the procedure of Example 1, except that each test contained the quantity of glucose oxidase indicated in Tables 2–8, below (instead of cholesterol oxidase as in Example 1), in an incubation medium of 5.6 mM glucose in 50 mM sodium acetate buffer containing 100 mEq/L of chloride and 0.1 mEq/L of bromide at pH 6. The potential amino acid activators indicated in Tables 2–8 below were added to the mixtures to a final concentration of 0, 5, 0.5 or 0.05 μmol/ml, and the incubation mixtures were innoculated with about $1 \times 10^7$ spores of *Aspergillus fumigatus*. The mixtures were incubated at ambient temperature for 90 minutes and then plated as described in Example 1. The plates were grown overnight at 35° C., and then for an additional two days. The colony forming units were counted as a measure of viability of the organisms.

The aliphatic amino acids glycine, l-alanine, l-valine, l-leucine and l-isoleucine were tested as described above. The results are shown in the following Table 2:

TABLE 2

Amino Acid Type and Concentration:
Effect on Haloperoxidase Killing of *Aspergillus fumigatus* Spores

| Haloperoxidase | Glucose Oxidase | (Amino Acid) μmol/ml (mM) | CFU (Aliphatic Amino Acids) | | | | |
|---|---|---|---|---|---|---|---|
| | | | Glycine | l-Alanine | l-Valine | l-Leucine | l-Isoleucine |
| 0 | 0 | 0 | 920,000 | 800,000 | 260,000 | 920,000 | 260,000 |
| 0 | 0 | 5 | 560,000 | 520,000 | 380,000 | 740,000 | 340,000 |
| 0 | 0 | 0.5 | 700,000 | 660,000 | 460,000 | 960,000 | 400,000 |
| 0 | 0 | 0.05 | 480,000 | 520,000 | 180,000 | 460,000 | 460,000 |
| 0 | 0.6 Units | 0 | 760,000 | 1,140,000 | 420,000 | 740,000 | 420,000 |
| 0 | 0.6 Units | 5 | 440,000 | 980,000 | 440,000 | 1,000,000 | 340,000 |
| 0 | 0.6 Units | 0.5 | 300,000 | 780,000 | 300,000 | 920,000 | 400,000 |
| 0 | 0.6 Units | 0.05 | 580,000 | 760,000 | 340,000 | 700,000 | 520,000 |
| 20 pmol MPO | 0.6 Units | 0 | 500,000 | 700,000 | 300,000 | 1,640,000 | 300,000 |
| 20 pmol MPO | 0.6 Units | 5 | 0 | 0 | 34,000 | 72,000 | 22,000 |
| 20 pmol MPO | 0.6 Units | 0.5 | 0 | 0 | 2,000 | 42,000 | 0 |
| 20 pmol MPO | 0.6 Units | 0.05 | 260,000 | 4,000 | 16,000 | 62,000 | 10,000 |
| 20 pmol EPO | 0.6 Units | 0 | 780,000 | 840,000 | 200,000 | 1,060,000 | 200,000 |
| 20 pmol EPO | 0.6 Units | 5 | 0 | 0 | 0 | 52,000 | 0 |
| 20 pmol EPO | 0.6 Units | 0.5 | 0 | 0 | 0 | 0 | 0 |
| 20 pmol EPO | 0.6 Units | 0.05 | 182,000 | 10,000 | 28,000 | 0 | 30,000 |

As shown in Table 2, each of the aliphatic amino acids tested exhibited a significant enhancing effect on the haloperoxidase antimicrobial activity of both eosinophil peroxidase and myeloperoxidase against *A. fumigatus* spores, with glycine and l-alanine exhibiting the greatest enhancing effect.

The dicarboxylic amino acids and amides l-aspartic acid, l-asparagine, l-glutamic acid and l-glutamine, and the imino acids l-proline and l-hydroxyproline were tested as described above. The results are shown in the following Table 3:

The hydroxyamino acids l-serine and l-threonine, and the basic amino acids l-lysine, l-histidine and l-arginine were tested as described above. The results are shown in the following Table 4:

TABLE 3

Amino Acid Type and Concentration: Effect on Haloperoxidase Killing of *Aspergillus fumigatus* Spores

| Haloperoxidase | Glucose Oxidase | (Amino Acid) μmol/ml (mM) | CFU (Dicarboxylic Amino Acids & Amides) | | | | CFU (Imino Acids) | |
|---|---|---|---|---|---|---|---|---|
| | | | l-Aspartic Acid | l-Asparagine | l-Glutamic Acid | l-Glutamine | l-Proline | l-Hydroxyproline |
| 0 | 0 | 0 | 520,000 | 520,000 | 920,000 | 920,000 | 260,000 | 860,000 |
| 0 | 0 | 5 | 540,000 | 540,000 | 260,000 | 420,000 | 420,000 | 640,000 |
| 0 | 0 | 0.5 | 460,000 | 180,000 | 320,000 | 660,000 | 300,000 | 800,000 |
| 0 | 0 | 0.05 | 200,000 | 240,000 | 580,000 | 300,000 | 480,000 | 740,000 |
| 0 | 0.6 Units | 0 | 340,000 | 340,000 | 740,000 | 740,000 | 420,000 | 740,000 |
| 0 | 0.6 Units | 5 | 420,000 | 340,000 | 280,000 | 400,000 | 240,000 | 540,000 |
| 0 | 0.6 Units | 0.5 | 360,000 | 460,000 | 340,000 | 360,000 | 360,000 | 460,000 |
| 0 | 0.6 Units | 0.05 | 380,000 | 160,000 | 640,000 | 560,000 | 200,000 | 720,000 |
| 20 pmol MPO | 0.6 Units | 0 | 700,000 | 700,000 | 1,640,000 | 1,640,000 | 300,000 | 940,000 |
| 20 pmol MPO | 0.6 Units | 5 | 640,000 | 660,000 | 840,000 | 1,080,000 | 540,000 | 1,000,000 |
| 20 pmol MPO | 0.6 Units | 0.5 | 960,000 | 340,000 | 820,000 | 1,000,000 | 380,000 | 900,000 |
| 20 pmol MPO | 0.6 Units | 0.05 | 800,000 | 680,000 | 820,000 | 750,000 | 280,000 | 680,000 |
| 20 pmol EPO | 0.6 Units | 0 | 920,000 | 920,000 | 1,060,000 | 1,060,000 | 200,000 | 860,000 |
| 20 pmol EPO | 0.6 Units | 5 | 920,000 | 1,340,000 | 1,100,000 | 820,000 | 280,000 | 840,000 |
| 20 pmol EPO | 0.6 Units | 0.5 | 1,460,000 | 440,000 | 540,000 | 660,000 | 460,000 | 1,260,000 |
| 20 pmol EPO | 0.6 Units | 0.05 | 620,000 | 1,260,000 | 900,000 | 400,000 | 380,000 | 680,000 |

As shown in Table 3, none of the dicarboxylic amino acids or imino acids tested exhibited a significant haloperoxidase antimicrobial activity enhancing effect at any of the concentrations tested.

TABLE 4

Amino Acid Type and Concentration: Effect on Haloperoxidase Killing of *Aspergillus fumigatus* Spores

| Haloperoxidase | Glucose Oxidase | (Amino Acid) μmol/ml (mM) | CFU (Hydroxyamino Acids) | | CFU (Basic Amino Acids) | | |
|---|---|---|---|---|---|---|---|
| | | | l-Serine | l-Threonine | l-Lysine | l-Histidine | l-Arginine |
| 0 | 0 | 0 | 800,000 | 760,000 | 520,000 | 700,000 | 800,000 |
| 0 | 0 | 5 | 820,000 | 520,000 | 520,000 | 440,000 | 780,000 |
| 0 | 0 | 0.5 | 540,000 | 800,000 | 460,000 | 840,000 | 740,000 |
| 0 | 0 | 0.05 | 580,000 | 660,000 | 460,000 | 840,000 | 620,000 |
| 0 | 0.6 Units | 0 | 1,140,000 | 400,000 | 340,000 | 400,000 | 1,140,000 |
| 0 | 0.6 Units | 5 | 480,000 | 800,000 | 240,000 | 520,000 | 580,000 |
| 0 | 0.6 Units | 0.5 | 620,000 | 360,000 | 480,000 | 740,000 | 960,000 |
| 0 | 0.6 Units | 0.05 | 640,000 | 560,000 | 520,000 | 560,000 | 1,020,000 |
| 20 pmol MPO | 0.6 Units | 0 | 700,000 | 500,000 | 700,000 | 500,000 | 700,000 |
| 20 pmol MPO | 0.6 Units | 5 | 700,000 | 400,000 | 380,000 | 720,000 | 960,000 |
| 20 pmol MPO | 0.6 Units | 0.5 | 660,000 | 0 | 0 | 640,000 | 740,000 |
| 20 pmol MPO | 0.6 Units | 0.05 | 560,000 | 12,000 | 0 | 520,000 | 840,000 |
| 20 pmol EPO | 0.6 Units | 0 | 840,000 | 780,000 | 920,000 | 780,000 | 840,000 |
| 20 pmol EPO | 0.6 Units | 5 | 0 | 1,000,000 | 560,000 | 740,000 | 960,000 |
| 20 pmol EPO | 0.6 Units | 0.5 | 34,000 | 0 | 620,000 | 600,000 | 700,000 |
| 20 pmol EPO | 0.6 Units | 0.05 | 860,000 | 40,000 | 920,000 | 102,000 | 900,000 |

As shown in Table 4, the hydroxyamino acids l-serine and l-threonine both significantly enhanced eosinoperoxidase killing of A. fumigatus spores while l-threonine and the basic amino acid l-lysine were effective in enhancing myeloperoxidase antimicrobial activity. The basic amino acids l-histidine and l-arginine exhibited no significant antimicrobial effects. Histidine is very reactive with singlet molecular oxygen, and as such, it would be expected to produce potent competitive inhibition of haloperoxidase action which might mask its capacity to stimulate spore germination.

The sulfur amino acids l-cysteine and l-methionine, and the aromatic amino acids l-phenylalanine, l-tyrosine and l-tryptophan were tested as described above. The results are shown in the following Table 5:

oxidase killing of A. fumigatus, while l-tryptophan exhibited no significant effect. These sulfur and aromatic amino acids are also relatively reactive with singlet molecular oxygen, and may competitively inhibit haloperoxidase action which would mask their capacity to stimulate spore germination. This might explain why l-phenylalanine and l-tyrosine are most effective when tested at a low concentration.

The effect of enantiomeric configuration of alanine and of isomeric configuration and derivatisation of alanine were tested as described above. The results are shown in the following Table 6:

TABLE 5

Amino Acid Type and Concentration: Effect on Haloperoxidase Killing of *Aspergillus fumigatus* Spores

| Haloperoxidase | Glucose Oxidase | (Amino Acid) μmol/ml (mM) | CFU (Sulfur Amino Acids) | | CFU (Aromatic Amino Acids) | | |
|---|---|---|---|---|---|---|---|
| | | | l-Cysteine | l-Methionine | l-Phenylalanine | l-Tyrosine | l-Tryptophan |
| 0 | 0 | 0 | 380,000 | 380,000 | 260,000 | 700,000 | 380,000 |
| 0 | 0 | 5 | 540,000 | 560,000 | 360,000 | 580,000 | 800,000 |
| 0 | 0 | 0.5 | 500,000 | 540,000 | 340,000 | 800,000 | 640,000 |
| 0 | 0 | 0.05 | 380,000 | 320,000 | 380,000 | 560,000 | 700,000 |
| 0 | 0.6 Units | 0 | 460,000 | 460,000 | 420,000 | 400,000 | 460,000 |
| 0 | 0.6 Units | 5 | 580,000 | 660,000 | 400,000 | 840,000 | 920,000 |
| 0 | 0.6 Units | 0.5 | 420,000 | 480,000 | 460,000 | 700,000 | 580,000 |
| 0 | 0.6 Units | 0.05 | 360,000 | 460,000 | 440,000 | 560,000 | 280,000 |
| 20 pmol MPO | 0.6 Units | 0 | 580,000 | 580,000 | 300,000 | 500,000 | 580,000 |
| 20 pmol MPO | 0.6 Units | 5 | 580,000 | 400,000 | 8,000 | 640,000 | 700,000 |
| 20 pmol MPO | 0.6 Units | 0.5 | 540,000 | 480,000 | 4,000 | 460,000 | 580,000 |
| 20 pmol MPO | 0.6 Units | 0.05 | 720,000 | 560,000 | 2,000 | 20,000 | 1,040,000 |
| 20 pmol EPO | 0.6 Units | 0 | 480,000 | 480,000 | 200,000 | 780,000 | 480,000 |
| 20 pmol EPO | 0.6 Units | 5 | 680,000 | 580,000 | 0 | 640,000 | 860,000 |
| 20 pmol EPO | 0.6 Units | 0.5 | 800,000 | 560,000 | 0 | 920,000 | 740,000 |
| 20 pmol EPO | 0.6 Units | 0.05 | 240,000 | 600,000 | 0 | 0 | 580,000 |

As shown in Table 5, the sulfur amino acids were ineffective in enhancing antimicrobial activity of either eosinophil peroxidase or myeloperoxidase. The aromatic amino acids l-phenylalanine and l-tyrosine both exhibited significant enhancement of eosinophil peroxidase and myeloper-

TABLE 6

Amino Acid Type and Concentration: Effect on Haloperoxidase Killing of *Aspergillus fumigatus* Spores

| Haloperoxidase | Glucose Oxidase | (Amino Acid) μmol/ml (mM) | CFU (Alinine Isomers and Derivatives) | | | | |
|---|---|---|---|---|---|---|---|
| | | | l-Alanine | d-Alanine | β-Alanine | l-Ala Methyl Ester | l-Ala-l-Ala |
| 0 | 0 | 0 | 800,000 | 740,000 | 740,000 | 740,000 | 740,000 |
| 0 | 0 | 5 | 520,000 | 720,000 | 580,000 | 500,000 | 660,000 |
| 0 | 0 | 0.5 | 660,000 | 760,000 | 920,000 | 540,000 | 640,000 |
| 0 | 0 | 0.05 | 520,000 | 760,000 | 740,000 | 540,000 | 620,000 |
| 0 | 0.6 Units | 0 | 1,140,000 | 760,000 | 760,000 | 760,000 | 760,000 |
| 0 | 0.6 Units | 5 | 980,000 | 660,000 | 900,000 | 860,000 | 780,000 |
| 0 | 0.6 Units | 0.5 | 780,000 | 700,000 | 620,000 | 740,000 | 680,000 |
| 0 | 0.6 Units | 0.05 | 760,000 | 600,000 | 860,000 | 1,200,000 | 360,000 |
| 20 pmol MPO | 0.6 Units | 0 | 700,000 | 820,000 | 820,000 | 820,000 | 820,000 |
| 20 pmol MPO | 0.6 Units | 5 | 0 | 14,000 | 760,000 | 0 | 660,000 |
| 20 pmol MPO | 0.6 Units | 0.5 | 0 | 0 | 900,000 | 0 | 500,000 |
| 20 pmol MPO | 0.6 Units | 0.05 | 4,000 | 10,000 | 1,116,000 | 440,000 | 480,000 |
| 20 pmol EPO | 0.6 Units | 0 | 840,000 | 1,020,000 | 1,020,000 | 1,020,000 | 1,020,000 |
| 20 pmol EPO | 0.6 Units | 5 | 0 | 0 | 940,000 | 0 | 660,000 |
| 20 pmol EPO | 0.6 Units | 0.5 | 0 | 0 | 880,000 | 0 | 1,360,000 |
| 20 pmol EPO | 0.6 Units | 0.05 | 10,000 | 10,000 | 720,000 | 580,000 | 680,000 |

As shown in Table 6, both the l- and d-enantiomers of alanine were highly effective in enhancing the myeloperoxidase and eosinophil peroxidase killing of *A. fumigatus*, while β-alanine exhibited no significant enhancing effect. Similarly, the methyl ester of l-alanine produced significant enhancement of antimicrobial activity. The l-alanine-l-alanine dipeptide exhibited no significant enhancement activity.

The effect of enantiomeric configuration of threonine was also tested as described above. The results are shown in the following Table 7:

TABLE 7

Amino Acid Type and Concentration: Effect on Haloperoxidase Killing of *Aspergillus fumigatus* Spores

| Haloperoxidase | Glucose Oxidase | (Amino Acid) µmol/ml (mM) | CFU (Enantiomers of Hydroxyamino Acids) | |
|---|---|---|---|---|
| | | | l-Threonine | d-Threonine |
| 0 | 0 | 0 | 760,000 | 800,000 |
| 0 | 0 | 5 | 520,000 | 820,000 |
| 0 | 0 | 0.5 | 800,000 | 760,000 |
| 0 | 0 | 0.05 | 660,000 | 680,000 |
| 0 | 0.6 Units | 0 | 400,000 | 1,140,000 |
| 0 | 0.6 Units | 5 | 800,000 | 460,000 |
| 0 | 0.6 Units | 0.5 | 360,000 | 720,000 |
| 0 | 0.6 Units | 0.05 | 560,000 | 720,000 |
| 20 pmol MPO | 0.6 Units | 0 | 500,000 | 700,000 |
| 20 pmol MPO | 0.6 Units | 5 | 400,000 | 420,000 |
| 20 pmol MPO | 0.6 Units | 0.5 | 0 | 0 |
| 20 pmol MPO | 0.6 Units | 0.05 | 12,000 | 280,000 |
| 20 pmol EPO | 0.6 Units | 0 | 780,000 | 840,000 |
| 20 pmol EPO | 0.6 Units | 5 | 1,000,000 | 0 |
| 20 pmol EPO | 0.6 Units | 0.5 | 0 | 0 |
| 20 pmol EPO | 0.6 Units | 0.05 | 40,000 | 520,000 |

As shown in Table 7, both the l- and d-enantiomers of threonine significantly enhanced the myeloperoxidase and eosinophil peroxidase killing of *A. fumigatus*.

The effect of using the α-keto acid forms of enhancing α-amino acids was tested with l-alanine and pyruvic acid, and with glycine and glyoxylic acid, as described above. The results are shown in the following Table 8:

As shown in Table 8, pyruvic acid and glyoxylic acid do not exhibit the activity enhancing effect of l-alanine and glycine.

Example 3

Effect of Antimicrobial Activity Enhancing Agents on Other Antifungal Systems

In order to determine the effect of l-alanine on the antimicrobial effect of the common antifungal compounds nystatin and amphotericin B, the procedure of Example 2 was followed using nystatin or amphotericin B in place of the haloperoxidase-glucose oxidase of Example 2 and 0 (control) or 10 µmol/ml of l-alanine with *Fusarium moniliforme* as the microbe. The results are shown in the following table 9:

TABLE 9

Effect of l-Alanine on Nystatin and Amphotericin B Antifungal Activity

| Antifungal Agent Final Concentration | l-Alanine µmol/test | CFU (*F. moniliforme* ATCC 38159) |
|---|---|---|
| None | None | 940,000 |
| Nystatin, 400 µg/ml | None | 120,000 |
| Nystatin, 40 µg/ml | None | 340,000 |
| Nystatin, 4 µg/ml | None | 500,000 |
| None | 10 | 1,020,000 |
| Nystatin, 400 µg/ml | 10 | 28,000 |
| Nystatin, 40 µg/ml | 10 | 124,000 |
| Nystatin, 4 µg/ml | 10 | 220,000 |
| None | None | 880,000 |
| Amphotericin B, 250 µg/ml | None | 320,000 |
| Amphotericin B, 25 µg/ml | None | 500,000 |
| Amphotericin B, 2.5 µg/ml | None | 880,000 |
| None | 10 | 840,000 |
| Amphotericin B, 250 µg/ml | 10 | 340,000 |
| Amphotericin B, 25 µg/ml | 10 | 460,000 |
| Amphotericin B, 2.5 µg/ml | 10 | 800,000 |

As can be seen in Table 9, the addition of l-alanine doubled the nystatin-dependent killing of *Fusarium moniliforme* but had no effect on amphotericin B-dependent killing of *Fusarium moniliforme*.

TABLE 8

Amino Acid Type and Concentration: Effect on Haloperoxidase Killing of *Aspergillus fumigatus* Spores

| Haloperoxidase | Glucose Oxidase | (Amino Acid) µmol/ml (mM) | CFU (Amino Acid versus Alpha Keto Acid) | | | |
|---|---|---|---|---|---|---|
| | | | l-Alanine | Pyruvic Acid | Glycine | Glyoxylic Acid |
| 0 | 0 | 0 | 800,000 | 860,000 | 860,000 | 860,000 |
| 0 | 0 | 5 | 520,000 | 880,000 | 720,000 | 600,000 |
| 0 | 0 | 0.5 | 660,000 | 700,000 | 480,000 | 700,000 |
| 0 | 0 | 0.05 | 520,000 | 660,000 | 640,000 | 560,000 |
| 0 | 0.6 Units | 0 | 1,140,000 | 740,000 | 740,000 | 740,000 |
| 0 | 0.6 Units | 5 | 980,000 | 760,000 | 520,000 | 560,000 |
| 0 | 0.6 Units | 0.5 | 780,000 | 600,000 | 760,000 | 600,000 |
| 0 | 0.6 Units | 0.05 | 760,000 | 480,000 | 800,000 | 660,000 |
| 20 pmol MPO | 0.6 Units | 0 | 700,000 | 940,000 | 940,000 | 940,000 |
| 20 pmol MPO | 0.6 Units | 5 | 0 | 820,000 | 0 | 1,060,000 |
| 20 pmol MPO | 0.6 Units | 0.5 | 0 | 880,000 | 0 | 660,000 |
| 20 pmol MPO | 0.6 Units | 0.05 | 4,000 | 580,000 | 90,000 | 580,000 |
| 20 pmol EPO | 0.6 Units | 0 | 840,000 | 860,000 | 860,000 | 660,000 |
| 20 pmol EPO | 0.6 Units | 5 | 0 | 640,000 | 0 | 740,000 |
| 20 pmol EPO | 0.6 Units | 0.5 | 0 | 560,000 | 0 | 720,000 |
| 20 pmol EPO | 0.6 Units | 0.05 | 10,000 | 780,000 | 460,000 | 740,000 |

The foregoing procedure was repeated using the antiseptic compounds hydrogen peroxide (H$_2$O$_2$) and sodium hypochlorite (NaClO) with spores of *Aspergillus fumigatus* and *Fusarium moniliforme*. The results are shown in the following Table 10:

TABLE 10

Effect of l-Alanine on Hydrogen Peroxide and Sodium Hypochlorite Antifungal Activity

| Antifungal Agent Final Concentration | l-Alanine μmol/test | CFU (*A. fumigatus* ATCC 10894) | CFU (*F. moniliforme* ATCC 38159) |
|---|---|---|---|
| None | None | 360,000 | 460,000 |
| H$_2$O$_2$, 3 mg/ml | None | 580,000 | 0 |
| H$_2$O$_2$, 0.3 mg/ml | None | 400,000 | 140,000 |
| H$_2$O$_2$, 0.03 mg/ml | None | 440,000 | 400,000 |
| H$_2$O$_2$, 0.003 mg/ml | None | 640,000 | 500,000 |
| None | 10 | 700,000 | 580,000 |
| H$_2$O$_2$, 3 mg/ml | 10 | 720,000 | 0 |
| H$_2$O$_2$, 0.3 mg/ml | 10 | 280,000 | 340,000 |
| H$_2$O$_2$, 0.03 mg/ml | 10 | 660,000 | 300,000 |
| H$_2$O$_2$, 0.003 mg/ml | 10 | 500,000 | 310,000 |
| None | None | 300,000 | 284,000 |
| NaClO, 1 mg/ml | None | 10,000 | 50,000 |
| NaClO, 0.1 mg/ml | None | 26,000 | 298,000 |
| NaClO 0.01 mg/ml | None | 560,000 | 290,000 |
| NaClO, 0.001 mg/ml | None | 640,000 | 294,000 |
| None | 10 | 700,000 | 380,000 |
| NaClO, 1 mg/ml | 10 | 26,000 | 292,000 |
| NaClO, 0.1 mg/ml | 10 | 54,000 | 404,000 |
| NaClO, 0.01 mg/ml | 10 | 580,000 | 404,000 |
| NaClO, 0.001 mg/ml | 10 | 280,000 | 304,000 | l-alanine and 2, 10 or 50 pmol of myeloperoxidase or eosinophil peroxidase per test against these organisms. The results are shown in the following Table 11 (*F. moniliforme*, ATCC #38159), Table 12 (*T. rubrum*, ATCC #28188, 18753 and 18758) and Table 13 (*C. neoformans*, ATCC #14115):

TABLE 11

Haloperoxidase Killing of *Fusarium moniliforme*

| Haloperoxidase | Glucose Oxidase | l-Alanine μmol/test | *Fusarium moniliforme* ATCC #38159 |
|---|---|---|---|
| None | None | 10 | 1,720,000 |
| None | 0.6 Units | None | 1,380,000 |
| None | 0.6 Units | 10 | 1,760,000 |
| 50 pmol MPO | None | 10 | 1,640,000 |
| 50 pmol MPO | 0.6 Units | None | 0 |
| 10 pmol MPO | 0.6 Units | None | 0 |
| 50 pmol MPO | 0.6 Units | 10 | 0 |
| 10 pmol MPO | 0.6 Units | 10 | 8,000 |
| 50 pmol EPO | None | 10 | 8,000 |
| 50 pmol EPO | 0.6 Units | None | 0 |
| 10 pmol EPO | 0.6 Units | None | 0 |
| 2 pmol EPO | 0.6 Units | None | 0 |
| 50 pmol EPO | 0.6 Units | 10 | 0 |
| 10 pmol EPO | 0.6 Units | 10 | 0 |
| 2 pmol EPO | 0.6 Units | 10 | 0 |

TABLE 12

Haloperoxidase Killing of Trichophyton

| Haloperoxidase | Glucose Oxidase | l-Alanine μmol/test | *Trichophyton rubrum* ATCC #28188 | *Trichophyton rubrum* ATCC #18753 | *Trichophyton rubrum* ATCC #18758 |
|---|---|---|---|---|---|
| None | None | 10 | 1,700,000 | 200,000 | 1,440,000 |
| None | 0.6 Units | 10 | 1,580,000 | 276,000 | 128,000 |
| 50 pmol MPO | None | 10 | 2,680,000 | 192,000 | 720,000 |
| 50 pmol MPO | 0.6 Units | None | 1,240,000 | 132,000 | 414,000 |
| 50 pmol MPO | 0.6 Units | 10 | 84,000 | 18,000 | 0 |
| 10 pmol MPO | 0.6 Units | 10 | 184,000 | 62,000 | 0 |
| 2 pmol MPO | 0.6 Units | 10 | 1,380,000 | 310,000 | 4,000 |
| 50 pmol EPO | None | 10 | 3,600,000 | 332,000 | 1,800,000 |
| 50 pmol EPO | 0.6 Units | None | 1,180,000 | 22,000 | 244,000 |
| 50 pmol EPO | 0.6 Units | 10 | 0 | 0 | 0 |
| 10 pmol EPO | 0.6 Units | 10 | 0 | 0 | 0 |
| 2 pmol EPO | 0.6 Units | 10 | 0 | 0 | 0 |

As with amphotericin B, no significant enhancement of hydrogen peroxide or hypochlorite antisepsis is seen when used in combination with l-alanine. In fact, l-alanine appears to inhibit peroxide and especially hypochlorite killing of the fungi. Under such conditions l-alanine probably acts as a competitive inhibitor.

Example 4

Effect of l-Alanine on Haloperoxidase Killing of Additional Organisms

The effect of l-alanine on the halperoxidase antimicrobial activity against *Fusarium moniliforme*, *Tricophyton rubrum* and *Crytococcus neoformans* was determined following the procedure of Example 2 using 0 (control) or 10 μmol/ml of

TABLE 13

Haloperoxidase Killing of *Cryptococcus neoformans*

| Haloperoxidase | Glucose Oxidase | l-Alanine μmol/test | CFU (*Cryptococcus neoformans*) ATCC #14115) |
|---|---|---|---|
| None | None | 10 | 960,000 |
| None | 0.6 Units | None | 680,000 |
| None | 0.6 Units | 10 | 480,000 |
| 50 pmol MPO | None | 10 | 480,000 |
| 50 pmol MPO | 0.6 Units | None | 480,000 |
| 50 pmol MPO | 0.6 Units | 10 | 440,000 |
| 10 pmol MPO | 0.6 Units | 10 | 860,000 |
| 2 pmol MPO | 0.6 Units | 10 | 220,000 |
| 50 pmol EPO | None | 10 | 660,000 |
| 50 pmol EPO | 0.6 Units | None | 460,000 |

TABLE 13-continued

Haloperoxidase Killing of *Cryptococcus neoformans*

| Haloperoxidase | Glucose Oxidase | l-Alanine μmol/test | CFU (*Cryptococcus neoformans*) ATCC #14115) |
|---|---|---|---|
| 50 pmol EPO | 0.6 Units | 10 | 0 |
| 10 pmol EPO | 0.6 Units | 10 | 0 |
| 2 pmol EPO | 0.6 Units | 10 | 640,000 |

As shown in Table 11, myeloperoxidase and eosinophil peroxidase are both highly effective against *Fusarium moniliforme* either in the presence or absence of l-alanine. In fact, EPO was found to be effective in the absence of glucose oxidase. As shown in Table 12, complete killing of Trichophyton is obtained with eosinophil peroxidase in the presence of l-alanine, while a significant enhancement of myeloperoxidase killing is obtained.

As shown in Table 13, l-alanine also significantly enhances eosinophil peroxidase killing of *Crytococcus neoformans*, while some enhancement in myeloperoxidase activity is seen.

Example 5

Effect of Cholesterol Oxidase Concentration on Oxidase-Haloperoxidase Microbicidal Action Against *Candida albicans*

The effect of cholesterol oxidase concentration on oxidase-haloperoxidase microbicidal action against *Candida albicans* was determined by following the procedure of Example 1, except that each test contained a different quantity of cholesterol oxidase from *Nocardia erythropolis* (0.1 unit=4 μg) as indicated, 10 pmol (1.4 μg) porcine MPO (ExOxEmis, Inc., San Antonio, Texas, U.S.A., Lot#1899201) or 10 pmol (0.7 μg) porcine EPO (ExOxEmis, Inc., San Antonio, Tex., U.S.A., Lot#1929201) in 50 mM Acetate Buffer containing 100 mEq/L Cl⁻, 1 mEq/L Br⁻, and 1 mM l-alanine. The pH was 6.7 with 50 mM MOPS as buffer. The final suspension contained 7 mM (7 μmol/ml) cholesterol in 8.5% ethanol. The final volume was 1 ml. After two hours incubation at 37° C., the microbes were plate on Sabouraud's dextrose agar. The results are expressed in Table 14 as the colony forming units (CFU) counted.

TABLE 14

Effect of Cholesterol Oxidase Concentration on Oxidase-Haloperoxidase Microbicidal Action Against *Candida albicans*:

| Organism | Cholesterol Oxidase | Haloperoxidase | CFU |
|---|---|---|---|
| Cand. albicans | None | None | 400,000 |
| Cand. albicans | 0.1 Unit | None | 480,000 |
| Cand. albicans | 0.1 Unit † | 10 pmol MPO | 420,000 |
| Cand. albicans | 0.1 Unit | 10 pmol MPO | 0 |
| Cand. albicans | 0.05 Unit | 10 pmol MPO | 0 |
| Cand. albicans | 0.025 Unit | 10 pmol MPO | 0 |
| Cand. albicans | 0.013 Unit | 10 pmol MPO | 76,000 |
| Cand. albicans | None | 10 pmol MPO | 560,000 |
| Cand. albicans | 0.1 Unit † | 10 pmol EPO | 400,000 |
| Cand. albicans | 0.1 Unit | 10 pmol EPO | 0 |
| Cand. albicans | 0.05 Unit | 10 pmol EPO | 0 |
| Cand. albicans | 0.025 Unit | 10 pmol EPO | 200 |
| Cand. albicans | 0.013 Unit | 10 pmol EPO | 180,000 |

TABLE 14-continued

Effect of Cholesterol Oxidase Concentration on Oxidase-Haloperoxidase Microbicidal Action Against *Candida albicans*:

| Organism | Cholesterol Oxidase | Haloperoxidase | CFU |
|---|---|---|---|
| Cand. albicans | None | 10 pmol EPO | 360,000 |

As shown in Table 14, complete killing of *C. albicans* was observed with 0.025 unit cholesterol oxidase plus 10 pmol MPO and 1 mM l-alanine. In the absence of l-alanine, no killing was observed with 0.1 unit cholesterol oxidase with 10 pmol MPO. Similar results were obtained with EPO was substituted as the haloperoxidase.

Example 6

Effect of Cholesterol Oxidase Concentration on Oxidase-Haloperoxidase Microbicidal Action Against Bacteria The procedure of Example 5 was followed using *Escherichia coli* in place of the *C. albicans* of Example 5. Each test contained the indicated quantity of cholesterol oxidase from *Nocardia erythropolis* (0.1 unit=4 μg), 10 pmol (1.4 μg) porcine MPO (ExOxEmis, Inc. San Antonio, Tex., U.S.A., Lot#1899201) or 10 pmol (0.7 μg) porcine EPO (ExOxEmis, Inc., San Antonio, Tex., U.S.A., Lot#1929201) in 50 mM Acetate Buffer containing 100 mEq/L Cl⁻, 1 mEq/L Br⁻, and 1 mM l-alanine. The pH was 6.7 with 50 mM MOPS as buffer. The final suspension contained 7 mM (7 μmol/ml) cholesterol in 8.5% ethanol. The final volume was 1 ml. After two hours incubation at 37° C., the microbes were plated on trypticase soy agar. The results are expressed in the following Table 15 as the colony forming units (CFU) counted.

TABLE 15

Effect of Cholesterol Oxidase Concentration on Oxidase-Haloperoxidase Microbicidal Action Against *Escherichia coli*:

| Organism | Cholesterol Oxidase | Haloperoxidase | CFU |
|---|---|---|---|
| Escherichia coli | None | None | 13,500,000 |
| Escherichia coli | 0.1 Unit | None | 2,300,000 |
| Escherichia coli | 0.1 Unit † | 10 pmol MPO | 0 |
| Escherichia coli | 0.1 Unit | 10 pmol MPO | 0 |
| Escherichia coli | 0.05 Unit | 10 pmol MPO | 0 |
| Escherichia coli | 0.025 Unit | 10 pmol MPO | 0 |
| Escherichia coli | 0.013 Unit | 10 pmol MPO | |
| Escherichia coli | None | 10 pmol MPO | 14,000,000 |
| Escherichia coli | 0.1 Unit † | 10 pmol EPO | 0 |
| Escherichia coli | 0.1 Unit | 10 pmol EPO | 0 |
| Escherichia coli | 0.05 Unit | 10 pmol EPO | 0 |
| Escherichia coli | 0.025 Unit | 10 pmol EPO | 0 |
| Escherichia coli | 0.013 Unit | 10 pmol EPO | 0 |
| Escherichia coli | None | 10 pmol EPO | 8,200,000 |

† indicates that the 50 mM Acetate Buffer did NOT contain l-alanine.

As shown in Table 15, complete MPO and EPO killing of *Escherichia coli* was observed at all cholesterol oxidase concentrations tested (0.0125 to 0.1 unit) in the absence or presence of 1 mM l-alanine. The same results were observed with *Staphylococcus aureus* (data not shown).

Example 7

Oxidase-Haloperoxidase Killing of Bacterial, Yeast and Fungal Spores Using Choline Oxidase The procedure of Example 1 was followed except that 0.2 unit choline oxidase was employed as the $H_2O_2$-generating oxidase. Where indicated the reaction contained 0.2 unit (i.e., 20 μg) choline oxidase from Alcaligenes sp., 20 pmol (2.8 μg) porcine MPO (ExOxEmis, Inc., San Antonio, Tex., U.S.A., Lot#1899201) or 20 pmol (1.5 μg) porcine EPO (ExOxEmis, Inc., San Antonio, Tex., U.S.A., Lot#1929201) in 50 mM Acetate Buffer containing 100 mEq/L Cl⁻, and 1 mEq/L Br⁻. The pH was 7 with 50 mM MOPS as buffer. The final concentration of choline was 150 mM (150 μmol/ml). The final volume was 1 ml. After four hours incubation at 22° C. the microbes were plated (*S. aureus* was plated on trypticase soy agar; *C. albicans* and *A. fumigatus* were plated on Sabouraud's dextrose agar). The results are expressed in Table 16 as the colony forming units (CFU) counted.

TABLE 16

Effect of l-Alanine on Choline Oxidase-Haloperoxidase Killing of *Staphylococcus aureus*, *Candida albicans*, and *Aspergillus fumigatus* Spores:

| Organism | Choline Oxidase | Haloperoxidase | CFU |
|---|---|---|---|
| Staph. aureus | None | None | 19,400,000 |
| Staph. aureus | 0.2 Unit | None | 13,800,000 |
| Staph. aureus | 0.2 Unit † | None | 15,400,000 |
| Staph. aureus | 0.2 Unit | 20 pmol MPO | 0 |
| Staph. aureus | 0.2 Unit † | 20 pmol MPO | 0 |
| Staph. aureus | 0.2 Unit | 20 pmol EPO | 0 |
| Staph. aureus | 0.2 Unit † | 20 pmol EPO | 0 |
| Cand. albicans | None | None | 1,460,000 |
| Cand. albicans | 0.2 Unit | None | 1,200,000 |
| Cand. albicans | 0.2 Unit † | None | 1,180,000 |
| Cand. albicans | 0.2 Unit | 20 pmol MPO | 1,120,000 |
| Cand. albicans | 0.2 Unit † | 20 pmol MPO | 0 |
| Cand. albicans | 0.2 Unit | 10 pmol EPO | 640,000 |
| Cand. albicans | 0.2 Unit † | 20 pmol EPO | 0 |
| Asperg. fumigatus | None | None | 1,260,000 |
| Asperg. fumigatus | 0.2 Unit | None | 1,260,000 |
| Asperg. fumigatus | 0.2 Unit † | None | 1,300,000 |
| Asperg. fumigatus | 0.2 Unit | 20 pmol MPO | 800,000 |
| Asperg. fumigatus | 0.2 Unit † | 20 pmol MPO | 0 |
| Asperg. fumigatus | 0.2 Unit | 20 pmol EPO | 740,000 |
| Asperg. fumigatus | 0.2 Unit † | 20 pmol EPO | 0 |

†indicates that the 50 mM Acetate Buffer contained 1 mM l-alanine.

Example 8

Oxidase-Haloperoxidase Killing of Bacterial, Yeast and Fungal Spores Using Lactate Oxidase The procedure of Example 7 was followed except that 0.2 unit lactate oxidase was employed as the $H_2O_2$-generating oxidase. Where indicated the reaction contained 0.2 unit (i.e., 5 μg) lactate oxidase from Pediococcus sp., 20 pmol (2.8 μg) porcine MPO (ExOxEmis, Inc., San Antonio, Tex., U.S.A., Lot#1899201) or 20 pmol (1.5 μg) porcine EPO (ExOxEmis, Inc., San Antonio, Tex., U.S.A., Lot#1929201) in 50 mM Acetate Buffer containing 100 mEq/L Cl⁻, and 1 mEq/L Br⁻. The pH was 7 with 50 mM MOPS as buffer. The final concentration of lactate was 150 mM (150 μmol/ml). The final volume was 1 ml. After four hours incubation (22° C.) the microbes were plated. *S. aureus* was plated on trypticase soy agar. *C. albicans* and *A. fumigatus* were plated on Sabouraud's dextrose agar. The results are expressed in Table 17 as the colony forming units (CFU) counted.

TABLE 17

Effect of l-Alanine on Lactate Oxidase-Haloperoxidase Killing of *Staphylococcus aureus*, *Candida albicans*, and *Aspergillus fumigatus* Spores:

| Organism | Lactate Oxidase | Haloperoxidase | CFU |
|---|---|---|---|
| Staph. aureus | None | None | 19,400,000 |
| Staph. aureus | 0.2 Unit | None | 23,400,000 |
| Staph. aureus | 0.2 Unit † | None | 24,400,000 |
| Staph. aureus | 0.2 Unit | 20 pmol MPO | 0 |
| Staph. aureus | 0.2 Unit † | 20 pmol MPO | 0 |
| Staph. aureus | 0.2 Unit | 20 pmol EPO | 0 |
| Staph. aureus | 0.2 Unit † | 20 pmol EPO | 0 |
| Cand. albicans | None | None | 1,460,000 |
| Cand. albicans | 0.2 Unit | None | 1,480,000 |
| Cand. albicans | 0.2 Unit † | None | 1,020,000 |
| Cand. albicans | 0.2 Unit | 20 pmol MPO | 1,380,000 |
| Cand. albicans | 0.2 Unit † | 20 pmol MPO | 1,500,000 |
| Cand. albicans | 0.2 Unit | 20 pmol EPO | 1,400,000 |
| Cand. albicans | 0.2 Unit † | 20 pmol EPO | 1,180,000 |
| Asperg. fumigatus | None | None | 1,260,000 |
| Asperg. fumigatus | 0.2 Unit | None | 860,000 |
| Asperg. fumigatus | 0.2 Unit † | None | 760,000 |
| Asperg. fumigatus | 0.2 Unit | 20 pmol MPO | 740,000 |
| Asperg. fumigatus | 0.2 Unit † | 20 pmol MPO | 400,000 |
| Asperg. fumigatus | 0.2 Unit | 20 pmol EPO | 760,000 |
| Asperg. fumigatus | 0.2 Unit † | 20 pmol EPO | 18,000 |

†indicates that the 50 mM Acetate Buffer contained 1 mM l-alanine.

Example 9

Oxidase-Haloperoxidase Killing of Bacterial, Yeast and Fungal Spores Using Alcohol Oxidase The procedure of Example 7 was followed except that 0.2 unit alcohol oxidase was employed as the $H_2O_2$-generating oxidase. Where indicated the reaction contained 0.2 unit (i.e., 21 μg) alcohol oxidase from *Candida boidinii*, 20 pmol (2.8 μg) porcine MPO (ExOxEmis, Inc., San Antonio, Tex., U.S.A., Lot#1899201) or 20 pmol (1.5 μg) porcine EPO (ExOxEmis, Inc., San Antonio, Tex., U.S.A., Lot#1929201) in 50 mM Acetate Buffer containing 100 mEq/L Cl⁻, and 1 mEq/L Br⁻. The pH was 7 with 50 mM MOPS as buffer. The final concentration of alcohol was 150 mM (150 μmol/ml). The final volume was 1 ml. After four hours incubation at 22° C. the microbes were plated. *S. aureus* was plated on trypticase soy agar. *C. albicans* and *A. fumigatus* were plated on Sabouraud's dextrose agar. The results are expressed in Table 18 as the colony forming units (CFU) counted.

TABLE 18

Effect of l-Alanine on Alcohol Oxidase-Haloperoxidase Killing of *Staphylococcus aureus*, *Candida albicans*, and *Aspergillus fumigatus* Spores:

| Organism | Alcohol Oxidase | Haloperoxidase | CFU |
|---|---|---|---|
| Staph. Aureus | None | None | 19,400,000 |
| Staph. Aureus | 0.2 Unit | None | 21,200,000 |
| Staph. Aureus | 0.2 Unit † | None | 19,400,000 |
| Staph. Aureus | 0.2 Unit | 20 pmol MPO | 840,000 |
| Staph. Aureus | 0.2 Unit † | 20 pmol MPO | 760,000 |
| Staph. Aureus | 0.2 Unit | 20 pmol EPO | 0 |
| Staph. Aureus | 0.2 Unit † | 10 pmol EPO | 0 |
| Cand. Albicans | None | None | 1,460,000 |
| Cand. Albicans | 0.2 Unit | None | 1,100,000 |
| Cand. Albicans | 0.2 Unit † | None | 1,460,000 |
| Cand. Albicans | 0.2 Unit | 20 pmol MPO | 1,180,000 |
| Cand. Albicans | 0.2 Unit † | 20 pmol MPO | 1,280,000 |

TABLE 18-continued

Effect of l-Alanine on Alcohol Oxidase-Haloperoxidase Killing of *Staphylococcus aureus*, *Candida albicans*, and *Aspergillus fumigatus* Spores:

| Organism | Alcohol Oxidase | Haloperoxidase | CFU |
|---|---|---|---|
| Cand. Albicans | 0.2 Unit | 20 pmol EPO | 1,220,000 |
| Cand. Albicans | 0.2 Unit † | 20 pmol EPO | 1,160,000 |
| Asperg. fumigatus | None | None | 1,260,000 |
| Asperg. fumigatus | 0.2 Unit | None | 620,000 |
| Asperg. fumigatus | 0.2 Unit † | None | 700,000 |
| Asperg. fumigatus | 0.2 Unit | 20 pmol MPO | 1,560,000 |
| Asperg. fumigatus | 0.2 Unit † | 20 pmol MPO | 320,000 |
| Asperg. fumigatus | 0.2 Unit | 20 pmol EPO | 1,040,000 |
| Asperg. fumigatus | 0.2 Unit † | 20 pmol EPO | 16,000 |

†indicates that the 50 mM Acetate Buffer contained 1 mM l-alanine.

Cholesterol oxidase (Table 1), choline oxidase (Table 16), and lactate oxidase (Table 17) in combination with either MPO or EPO produced complete killing of *Staphylococcus aureus* in the presence or absence of l-alanine. With alcohol oxidase (Table 18), killing was complete with EPO, but only partial with MPO either with or without l-alanine.

*Candida albicans* was totally killed by cholesterol oxidase (Table 1) and choline oxidase (Table 16) plus MPO or EPO only in the presence of l-alanine. In the absence of l-alanine, microbicidal action was limited to approximately fifty percent kill. Lactate oxidase (Table 17) and alcohol oxidase (Table 18) were not effective in driving MPO or EPO killing of *Candida albicans* in the presence or absence of l-alanine.

In the presence of l-alanine, both cholesterol oxidase (Table 1) and choline oxidase (Table 16) supported complete killing of *Aspergillus fumigatus* spores by MPO or EPO. However, only partial killing was observed in the absence of l-alanine. Although incomplete, both lactate oxidase (Table 17) and alcohol oxidase (Table 18) produced greater than 90% spore kill with EPO and greater than 50% spore kill with MPO in the presence of l-alanine. In the absence of l-alanine, neither lactate oxidase or alcohol oxidase supported MPO or EPO killing of *Aspergillus fumigatus* spores.

Example 10

The Effect of Potential Activator Substances on Cholesterol Oxidase-Haloperoxidase Killing of Bacillus and Aspergillus Spores.

The microbiology literature describes several substances that might serve as activators of germination of spores and vegetative forms. Conidiospore germination has been reported to require glucose, phosphate and an amino acid. L-proline or l-alanine fulfill the amino acid requirement. Other amino acids and vitamins are less effective (Yanigita, 1957, Arch Mikrobiol 26:329).

Several other organic compounds have been reported to stimulate germination. These include phenethyl alcohol (Lingappa et al., 1970, Arch Mikrobiol 72:97), coumarin (Weber and Hess, 1974, The Fungal Spore, p. 178, Wiley-Interscience), and furfural derivatives (Sussman et al., 1959, Mycologia 51:237).

The effect of l-alanine and l-proline on cholesterol oxidase-haloperoxidase killing of *Bacillus cereus* endospores contained 0.1 unit (i.e., 4 µg) cholesterol oxidase from *Nocardia erythropolis*, 20 pmol (2.8 µg) porcine MPO (ExOxEmis, Inc., San Antonio, Tex., U. S. A., Lot#1899201) or 20 pmol (1.5 µg) porcine EPO (ExOxEmis, Inc., San Antonio, Tex., U. S. A., Lot#1929201), and the indicated quantity of l-alanine or l-proline in 50 mM Acetate Buffer containing 100 mEq/L $Cl^-$, and 1 mEq/L $Br^-$. The pH was adjusted to ~7 by addition of 50 mM MOPS buffer. The final concentration of cholesterol was 5 mM (5 µmol/ml) in 8.5% ethanol. The final volume was 1 ml. After the indicated period of incubation (22° C.), the surviving microbes were plated on trypticase soy agar. The results are shown in Table 19 as the colony forming units (CFU) counted.

TABLE 19

Effects of l-Alanine and l-Proline on Cholesterol Oxidase-Haloperoxidase Microbicidal Action Against *Bacillus cereus* Spores:

| Treatment: Haloperoxidase | Activator Substance | *Bacillus cereus* Survival, CFU (Post Exposure Time in Hours) | | | | |
|---|---|---|---|---|---|---|
| | | 0.5 Hr. | 1 Hr. | 1.5 Hr. | 2 Hrs. | 3 Hrs. |
| None | None | 900,000 | 460,000 | 720,000 | 720,000 | 520,000 |
| None | l-alanine, 10 µmol | 860,000 | 660,000 | 560,000 | 520,000 | 400,000 |
| None | l-proline, 10 µmol | 820,000 | 760,000 | 620,000 | 320,000 | 540,000 |
| MPO, 20 pmol | None | 0 | 0 | 0 | 0 | 0 |
| MPO, 20 pmol | l-alanine, 10 µmol | 0 | 0 | 0 | 0 | 0 |
| MPO, 20 pmol | l-proline, 10 µmol | 0 | 0 | 0 | 0 | 0 |
| EPO, 20 pmol | None | 2,000 | 2,000 | 0 | 0 | 0 |
| EPO, 20 pmol | l-alanine, 10 µmol | 2,000 | 0 | 0 | 0 | 0 |
| EPO, 20 pmol | l-proline, 10 µmol | 0 | 2,000 | 0 | 0 | 0 |

After thirty minutes of incubation, cholesterol oxidase (0.1 unit) with MPO (20 pmol) produced complete killing of *Bacillus cereus* spores with either l-alanine or l-proline as the activator. However, killing was also complete without any added enhancer substance. Although a longer incubation period was required, similar results were obtained using cholesterol oxidase with EPO. In the absence of haloperoxidase, addition of l-alanine or l-proline did not significantly increase killing activity of cholesterol oxidase. The direct sensitivity of these bacterial endospores to the oxidase-haloperoxidase killing is so great that any effect of l-alanine or l-proline is hidden in the total kill observed as early as thirty minutes.

The effect of l-alanine, l-proline, coumarin, and phenethyl alcohol on cholesterol oxidase-haloperoxidase killing of *Aspergillus fumigatus* spores was determined by following the foregoing procedure except that the reaction contained 0.1 unit (i.e., 4 µg) cholesterol oxidase from *Nocardia erythropolis*, 20 pmol (2.8 µg) porcine MPO (ExOxEmis, Inc., San Antonio, Tex., U. S. A., Lot#1899201) or 20 pmol (1.5 µg) porcine EPO (ExOxEmis, Inc., San Antonio, Tex., U. S. A., Lot#1929201), and the indicated quantity of substance to be tested in 50 mM Acetate Buffer containing 100 mEq/L Cl$^-$, and 1 mEq/L Br$^-$. The pH was adjusted to ~7 by addition of 50 mM MOPS buffer. The final concentration of cholesterol was 5 mM (5 µmol/ml) in 8.5% ethanol. The final volume was 1 ml. After the indicated period of incubation (37° C.), Aspergillus fumigatus was plated on Sabouraud's dextrose agar. The results are expressed in Table 20 as the colony forming units (CFU) counted. PEA is the acronym for phenethyl alcohol. Of the four potential activator substances tested, 1-alanine alone increased the kill capacity of cholesterol oxidase with either MPO or EPO. In the absence of haloperoxidase, none of the activators increased the killing activity of cholesterol oxidase.

microbial activity enhancing agent 1-alanine, and (2) cholesterol in the form of a solid wafer. The cholesterol wafers were prepared by dissolving cholesterol in ether, pouring the cholesterol solution on a surface, and allowing the ether to evaporate. The resulting sheet of cholesterol was cut into appropriately sized rectangles of approximately 10 mg.

Cholesterol wafers (approximately 10 mg/wafer) were placed in test tubes containing Aspergillus fumigatus spores. Cholesterol oxidase with and without MPO or EPO was added to the tubes to initiate fungicidal action. The system was tested with and without 1-alanine, and with and without ethanol. Ethanol was added to test its capacity to facilitate cholesterol solubilization. Increased cholesterol solubility would mean increased cholesterol available as substrate for the oxidase. Once initiated, the system was allowed to incubate at ambient temperature (22° C.) for time intervals ranging from thirty minutes to four hours. The reaction

TABLE 20

Effects of 1-Alanine, 1-Proline, Coumarin, and Phenethyl Alcohol on Cholesterol Oxidase-Haloperoxidase Microbicidal Action Against *Aspergillus fumigatus* Spores:

| Treatment: Haloperoxidase | Activator Substance | A. fumigatus Survival, CFU (Post Exposure Time in Hours) | | | | |
|---|---|---|---|---|---|---|
| | | 1 Hr. | 1.5 Hr. | 2 Hrs. | 3 Hrs. | 4 Hrs. |
| None | None | 710,000 | 760,000 | 530,000 | 340,000 | 240,000 |
| None | 1-alanine, 10 µmol | 780,000 | 720,000 | 500,000 | 340,000 | 340,000 |
| None | 1-proline, 10 µmol | 900,000 | 540,000 | 560,000 | 400,000 | 200,000 |
| None | coumarin, 1 µmol | 320,000 | 700,000 | 480,000 | 240,000 | 500,000 |
| None | PEA, 5 µmol | 380,000 | 600,000 | 360,000 | 440,000 | 480,000 |
| MPO, 20 pmol | None | 520,000 | 940,000 | 500,000 | 410,000 | 550,000 |
| MPO, 20 pmol | 1-alanine, 10 µmol | 0 | 0 | 0 | 0 | 0 |
| MPO, 20 pmol | 1-proline, 10 µmol | 8360,000 | 880,000 | 760,000 | 700,000 | 260,000 |
| MPO, 20 pmol | coumarin, 1 µmol | 740,000 | 620,000 | 500,000 | 620,000 | 660,000 |
| MPO, 20 pmol | PEA, 5 µmol | 500,000 | 600,000 | 420,000 | 420,000 | 520,000 |
| EPO, 20 pmol | None | 920,000 | 690,000 | 440,000 | 710,000 | 760,000 |
| EPO, 20 pmol | 1-alanine, 10 µmol | 0 | 0 | 0 | 0 | 0 |
| EPO, 20 pmol | 1-proline, 10 µmol | 1,100,000 | 840,000 | 1,000,000 | 500,000 | 520,000 |
| EPO, 20 pmol | coumarin, 1 µmol | 760,000 | 780,000 | 420,000 | 340,000 | 300,000 |
| EPO, 20 pmol | PEA, 5 µmol | 780,000 | 600,000 | 480,000 | 460,000 | 320,000 |

Incorporation of 1-alanine into the formulation greatly increases the fungicidal action of oxidase-haloperoxidase against both spores and vegetative forms. L-alanine appears to provide the amine nitrogen, $CO_2$, acetyl-CoA, and reducing equivalents required for germination and growth and as such labilizes the fungi to the action of haloperoxidases. As previously shown with haloperoxidase-glucose oxidase killing (Table 3), 1-proline is not effective as an enhancer substance.

Example 11

Binary Antiseptic Consisting of (1) Cholesterol Oxidase-Haloperoxidase and (2) Cholesterol in Solid Form.

The cholesterol oxidase-haloperoxidase system was constructed as a binary formulation consisting of: (1) a solution containing cholesterol oxidase-haloperoxidase plus the anti-microbial activity enhancing agent 1-alanine, and (2) cholesterol in the form of a solid wafer.

contained 0.1 units (i.e., 4 µg) cholesterol oxidase from *Nocardia erythropolis*, 10 pmol (1.4 µg) porcine MPO (ExOxEmis, Inc., San Antonio, Tex., U. S. A., Lot#1899201) or 10 pmol (0.7 µg) porcine EPO (ExOxEmis, Inc., San Antonio, Tex. U. S. A., Lot#1929201) in 50 mM Acetate Buffer containing 100 mEq/L Cl$^-$, and 1 mEq/L Br$^-$. The pH was adjusted to ~7 by addition of 50 mM MOPS buffer. The substrate cholesterol was present in the form of a solid wafer (approximately 10 mg). Where indicated the reaction contained 10 µmol/ml 1-alanine and 10% ethanol. The final volume was 1 ml. After the indicated period of incubation (22° C.), *Aspergillus fumigatus* was plated on Sabouraud's dextrose agar. The results are expressed as the colony forming units (CFU's) counted. ND indicates that the experiment was not done. The results are presented in Table 21.

TABLE 21

Effects of l-Alanine on Cholesterol Oxidase-Haloperoxidase Microbicidal Action Against *Aspergillus fumigatus* Spores Using Solid Cholesterol as Substrate With and Without Ethanol:

| Treatment: | | | A. fumigatus Survival, CFU (Post Exposure Time in Hours) | | | |
|---|---|---|---|---|---|---|
| Haloperoxidase | l-Alanine | Ethanol | 0.5 Hr | 1 Hrs. | 2 Hrs. | 4 Hrs. |
| None | None | 10% | 960,000 | 1,900,000 | 960,000 | 800,000 |
| None | 10 μmol | 10% | 1,180,000 | 1,220,000 | 820,000 | 158,000 |
| MPO, 10 pmol | None | 10% | 920,000 | 1,540,000 | 1,120,000 | 1,020,000 |
| MPO, 10 pmol | 10 μmol | 10% | 82,000 | 0 | 0 | 0 |
| EPO, 10 pmol | None | 10% | 1,120,000 | 3,000,000 | 040,000 | 940,000 |
| EPO, 10 pmol | 10 μmol | 10% | 0 | 0 | 0 | 0 |
| None | None | None | ND | 2,300,000 | ND | 980,000 |
| None | 10 μmol | None | ND | 1,980,000 | ND | 1,900,000 |
| MPO, 10 pmol | None | None | ND | 2,380,000 | ND | 1,860,000 |
| MPO, 10 pmol | 10 μmol | None | ND | 1,640,000 | ND | 10,000 |
| EPO, 10 pmol | None | None | ND | 2,620,000 | ND | 1,340,000 |
| EPO, 10 pmol | 10 μmol | None | ND | 1,340,000 | ND | 0 |

As shown in Table 21, in the presence of ethanol plus l-alanine, the cholesterol oxidase-MPO formulation effected a tenfold killing of the spores at thirty minutes and complete killing at one, two, and four hours. L-alanine was required for effective MPO-dependent killing. In the presence of ethanol and l-alanine but absence of haloperoxidase, cholesterol oxidase was mildly effective but only after four hours incubation. The most effective formulation was cholesterol oxidase-EPO with ethanol and l-alanine. Complete spore killing was observed for all test intervals.

Inclusion of ethanol greatly increased the effectiveness of all the formulations tested. Sporadical action is faster and more intense in the presence of 10% ethanol. This ethanol effect may result from increased solubilization of the solid cholesterol resulting in increased cholesterol oxidase activity. The results also demonstrate that 10% ethanol has no detrimental effect on the cholesterol oxidase-haloperoxidase function. Inclusion of an adequate quantity of ethanol or other nontoxic solvent in the formulation also assists in maintaining sterility of the system in the absence of cholesterol and improves the shelf-life of the reaction mixture.

Various modifications and adaptations of the methods and compositions of the invention will be apparent from the foregoing to those skilled in the art. Any such modifications and adaptations are intended to be within the scope of the appended claims except insofar as precluded by the prior art.

I claim:

1. A method for killing or inhibiting the growth of sporulating microorganisms selected from the group consisting of bacteria, yeast or fungi, in a subject in need thereof, comprising:

administering, in the presence of a halide selected from the group consisting of chloride or bromide, an antimicrobially effective amount of a composition comprising a haloperoxidase and at least one agent of the formula:

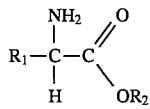

wherein $R_1$ is hydrogen, an unsubstituted, or hydroxy or amino substituted, straight or branched chain alkyl group having from 1 to 6 carbon atoms, and $R_2$ is hydrogen or a straight or branched chain alkyl group having from 1 to 6 carbon atoms; wherein said composition is administered by directly contacting said composition with the sporulating microorganism.

2. The method of claim 1 wherein the haloperoxidase is selected from the group consisting of myeloperoxidase, eosinophil peroxidase and combinations thereof.

3. The method of claim 2 wherein the haloperoxidase is myeloperoxidase.

4. The method of claim 3 wherein the composition comprises at least 0.01 pmol/ml of myeloperoxidase in a liquid carrier.

5. The method of claim 4 wherein the composition comprises from 0.1 pmol/ml to 500 pmol/ml of myeloperoxidase.

6. The method of claim 4 wherein the composition comprises from 0.5 pmol/ml to 50 pmol/ml of myeloperoxidase.

7. The method of claim 2 wherein the haloperoxidase is eosinophil peroxidase.

8. The method of claim 7 wherein the composition comprises at least 0.01 pmol of eosinophil peroxidase in a liquid carrier.

9. The method of claim 8 wherein the composition comprises from 0.1 pmol to 500 pmol per ml of eosinophil peroxidase in a liquid carrier.

10. The method of claim 8 wherein the composition comprises from 0.5 pmol/ml to 50 pmol/ml of eosinophil peroxidase.

11. The method of claim 8 wherein the composition further comprises from 10 nmol/ml to 10 μmol/ml of bromide.

12. The method of claim 1 wherein said agent is an α-amino acid selected from the group consisting of glycine, alanine, valine, leucine, isoleucine, serine, threonine, lysine, and the alkyl esters of any of the members of the group.

13. The method of claim 12 wherein the composition comprises at least 0.005 μmol/ml of said agent in a liquid carrier.

14. The method of claim 13 wherein the composition comprises from 0.05 μmol/ml to 50 μmol/ml of said agent in a liquid carrier.

15. The method of claim 1 wherein the composition further comprises hydrogen peroxide or an oxidase that produces a peroxide in the presence of a substrate for the oxidase.

16. The method of claim 15 wherein the composition comprises a peroxide producing oxidase effective to generate from 100 pmol to 50 μmol peroxide per ml per minute when in the presence of a substrate for the oxidase.

* * * * *

UNITED STATES PATENT AND TRADEMARK OFFICE
CERTIFICATE OF CORRECTION

PATENT NO. : 5,510,104
DATED : April 23, 1996
INVENTOR(S) : R.C. Allen

It is certified that error appears in the above-indentified patent and that said Letters Patent is hereby corrected as shown below:

On the title page:

| [54] | Title | "INHABITING" should read --INHIBITING-- |
| [56] | Refs. Cited | After "Allen" delete --et al.-- |
| [56] | Refs. Cited | ""Evaulation" should read --"Evaluation-- |
| [56] | Refs. Cited | "Chemiluminescence;" should read --Chemiluminescence:-- |
| [56] | Refs. Cited | "Liquid Scintillation . . . pp. 377-393." should not be |
| [56] | Refs. Cited | After "35" insert --,-- |
| [56] | Refs. Cited | "Ligan-d-Receptor" should read --Ligand-Receptor-- |
| [56] | Refs. Cited | "193-219," should read --193-210,-- |

UNITED STATES PATENT AND TRADEMARK OFFICE
CERTIFICATE OF CORRECTION

PATENT NO. : 5,510,104
DATED : April 23, 1996
INVENTOR(S) : R.C. Allen

Page 2 of 6

It is certified that error appears in the above-indentified patent and that said Letters Patent is hereby corrected as shown below:

On the title page:

| | | |
|---|---|---|
| [56] | Refs. Cited | "Systems,"," should read --Systems",-- |
| [56] | Refs. Cited | "mitis-dependent antimicrobial system in saliva"," should not be italicized. |
| [56] | Refs. Cited | After "*gen*" insert --.-- |
| [56] | Refs. Cited | After "21" insert --,-- |
| [56] | Refs. Cited | "*Nocardia sp.*" should read --*Nocardia* sp.-- |
| [56] | Refs. Cited | "System"" should read --System,"-- |
| [56] | Refs. Cited | "Antimicrobia" should read --Antimicrobial-- |

| Column | line | |
|---|---|---|
| 1 | 1 | "INHABITING" should read --INHIBITING-- |
| 1 | 32 | "of" should read --or-- |

UNITED STATES PATENT AND TRADEMARK OFFICE
CERTIFICATE OF CORRECTION

PATENT NO. : 5,510,104
DATED : April 23, 1996
INVENTOR(S) : R.C. Allen

It is certified that error appears in the above-indentified patent and that said Letters Patent is hereby corrected as shown below:

| COLUMN | LINE | |
|---|---|---|
| 2 | 27 | "Tranamination" should read --Transamination-- |
| 2 | 49 | After "J" insert --.-- |
| 6 | 29 | "R+H>>$CH_3$>$CH_3CH_2$>$CH_3(CH_2)_2$" should read --R=H>>$CH_3$>$CH_3CH_2$>$CH_3(CH_2)_2$-- |
| 7 | 32 | After "oxidase" insert --.-- |
| 7 | 63 | "halide peroxide" should read --halide:peroxide-- |
| 10 | 54 | After "Tex." insert --,-- |
| 10 | 57 | "$Cl^{31}$," should read --$Cl^-$,-- |
| 14 (TABLE 4, | 52 line 5 of text) | Under "l-Histidine," "700,000" should read --760,000-- |
| 14 (TABLE 4, | 53 line 6 of text) | Under "l-Arginine," "780.000" should read --780,000-- |
| 16 (TABLE 5, | 24 line 5 of text) | Under "l-Tyrosine," "700,000" should read --760,000-- |
| 18 (TABLE 8, | 60 line 16 of text) | Under "Glyoxylic Acid," "660,000" should read --860,000-- |

UNITED STATES PATENT AND TRADEMARK OFFICE
CERTIFICATE OF CORRECTION

PATENT NO. : 5,510,104
DATED : April 23, 1996
INVENTOR(S) : R.C. Allen

It is certified that error appears in the above-indentified patent and that said Letters Patent is hereby corrected as shown below:

| COLUMN | LINE | |
|---|---|---|
| 18 (TABLE 8, | 62 line 18 of text) | Under "Glyoxylic Acid," "660,000" should read --860,000-- |
| 18 | 17 | "table 9:" should read --Table 9:-- |
| 19 | 3 | "with spores" should read --with the spores-- |
| 20 (TABLE 12, | 36 line 2 of text) | "Trichophyton" should be italicized. |
| 21 | 16-17 | "Trichophyton" should be italicized. |
| 21 | 21 | "*Crytococcus*" should read --*Cryptococcus*-- |
| 21 | 45 | "plate" should read --plated-- |
| 22 | 10 | At the bottom of TABLE 14 (continued) insert --† indicates that the 50mM Acetate Buffer did NOT contain *l*-alanine.-- |
| 22 | 15 | "with" should read --when-- |
| 22 | 30 | After "Inc." insert --,-- |
| 23 | 8 | "Alcaligenes sp." should be italicized. |

UNITED STATES PATENT AND TRADEMARK OFFICE
CERTIFICATE OF CORRECTION

PATENT NO. : 5,510,104
DATED : April 23, 1996
INVENTOR(S) : R.C. Allen

It is certified that error appears in the above-indentified patent and that said Letters Patent is hereby corrected as shown below:

| COLUMN | LINE | |
|---|---|---|
| 23 (TABLE 16, | 39 line 19 of text) | Under "Haloperoxidase," "10 pmol EPO" should read --20 pmol EPO-- |
| 23 | 57 | "Pediococcus sp." should be italicized. |
| 24 (TABLE 18, | 62 line 13 of text) | Under "Haloperoxidase," "10 pmol EPO" should read --20 pmol EPO-- |
| 27 (TABLE 20, | 35 line 15 of text) | Under "1 Hr.," "8360,000" should read --860,000-- |
| 27 (TABLE 20, | 38 line 18 of text) | Under "2 Hrs.," "440,000" should read --840,000-- |

UNITED STATES PATENT AND TRADEMARK OFFICE
CERTIFICATE OF CORRECTION

PATENT NO. : 5,510,104
DATED : April 23, 1996
INVENTOR(S) : R.C. Allen

It is certified that error appears in the above-indentified patent and that said Letters Patent is hereby corrected as shown below:

| COLUMN | LINE | |
|---|---|---|
| 28 | 49 | After "Tex." insert --,-- |
| 29 (TABLE 21, | 14 line 12 of text) | Under "2 Hrs.," "040,000" should read --3,040,000-- |

Signed and Sealed this

Fourteenth Day of January, 1997

Attest:

BRUCE LEHMAN

*Attesting Officer*     *Commissioner of Patents and Trademarks*